US006878815B2

(12) United States Patent
Erikson et al.

(10) Patent No.: US 6,878,815 B2
(45) Date of Patent: Apr. 12, 2005

(54) HETEROPOLYMERIC TRIPLEXES CONTAINING WATSON-CRICK TRIPLETS

(75) Inventors: Glen H. Erikson, Providenciales (TC); Jasmine I. Daksis, Richmond Hill (CA); Pierre Picard, Ottawa (CA)

(73) Assignee: Ingeneus Corporation, Bridgetown (BB)

( * ) Notice: Subject to any disclaimer, the term of this patent is extended or adjusted under 35 U.S.C. 154(b) by 22 days.

(21) Appl. No.: 10/103,002

(22) Filed: Mar. 21, 2002

(65) Prior Publication Data

US 2002/0173480 A1 Nov. 21, 2002

Related U.S. Application Data

(60) Division of application No. 09/613,263, filed on Jul. 10, 2000, now Pat. No. 6,420,115, which is a continuation-in-part of application No. 09/468,679, filed on Dec. 21, 1999, now Pat. No. 6,403,313.

(51) Int. Cl.[7] ............................ C07H 21/04; C12Q 1/68
(52) U.S. Cl. .................. 536/23.1; 536/24.3; 536/24.31; 536/24.32; 536/24.33; 435/6
(58) Field of Search .......................... 435/6, 91.1, 91.2, 435/91.21, 287.2; 536/24.3, 25.32

(56) References Cited

U.S. PATENT DOCUMENTS

| | | |
|---|---|---|
| 4,876,187 A | 10/1989 | Duck et al. |
| 4,963,477 A | 10/1990 | Tchen |
| 5,011,769 A | 4/1991 | Duck et al. |
| 5,403,711 A | 4/1995 | Walder et al. |
| 5,539,082 A | 7/1996 | Nielsen et al. |
| 5,558,998 A | 9/1996 | Hammond et al. |
| 5,660,988 A | 8/1997 | Duck et al. |
| 5,705,346 A | 1/1998 | Okamoto et al. |
| 5,707,801 A | 1/1998 | Bresser et al. |
| 5,731,146 A | 3/1998 | Duck et al. |
| 5,800,984 A | 9/1998 | Vary |
| 5,800,992 A | 9/1998 | Fodor et al. |
| 5,814,516 A | 9/1998 | Vo-Dinh |
| 5,824,477 A | 10/1998 | Stanley |
| 5,861,124 A | 1/1999 | Hosoi et al. |
| 5,888,739 A | 3/1999 | Pitner et al. |
| 5,912,332 A | 6/1999 | Agrawal et al. |
| 5,948,897 A | 9/1999 | Sen et al. |
| 6,013,442 A | 1/2000 | Kolesar et al. |
| 6,017,709 A | 1/2000 | Hardin et al. |
| 6,027,880 A | 2/2000 | Cronin et al. |
| 6,046,004 A | 4/2000 | Wu et al. |
| 6,048,690 A | 4/2000 | Heller et al. |
| 6,060,242 A | 5/2000 | Nie et al. |
| 6,107,078 A | 8/2000 | Keese et al. |
| 6,117,657 A | 9/2000 | Usman et al. |
| 6,251,591 B1 | 6/2001 | Wu et al. |
| 6,255,050 B1 | 7/2001 | Nie et al. |
| 6,255,469 B1 | 7/2001 | Seeman et al. |
| 6,265,170 B1 | 7/2001 | Picard et al. |
| 6,287,772 B1 | 9/2001 | Stefano et al. |
| 6,312,925 B1 | 11/2001 | Meyer, Jr. et al. |

FOREIGN PATENT DOCUMENTS

| | | |
|---|---|---|
| GB | 2333359 A | 7/1999 |
| WO | WO 97/45539 A1 | 12/1997 |
| WO | 2338301 A | 12/1999 |
| WO | WO 00/20633 A1 | 4/2000 |

OTHER PUBLICATIONS

Baran et al., *Nucleic Acids Research* 25:297–303 (1997).
Bohmann et al., *Science*, 238:1386–1392 (Dec. 1987).
Chan et al., *J. Mol. Med.* 75 Issue 4:267–282 (1997).
Dalrymple et al., *Nucleic Acids Research*, vol. 13, No. 21, pp. 7865–7879 (1985).
Hill et al., *Methods in Enzymology*, 278:390–416 (1997).
Johansen and Jacobsen, *J Biomol Struct Dyn*, 16(2):205–22 (Oct. 1998) (Abstract).
Kadonaga et al., *Cell*, 51:1079–1090 (Dec. 24, 1987).
Kukreti et al. 25 *Nucleic Acids Research* 4264–4270 (1997).
Marsh et al., *Nucleic Acids Research*, 23:696–700 (1995).
Marsh et al., *Biochemistry* 33:10718–10724 (1994).
Mazumder et al., *Biochemistry* 35:13762–13771 (1996).
Sen et al., *Nature* 334:364–366 (Jul. 28, 1988).
Sen et al., *Biochemistry* 31:65–70 (1992).
Sturm et al., *Genes & Development*, 2:1582–1599 (1988).
Watson, James, "A Personal Account of the Discovery of the Structure of DNA," (1968).
Williamson et al., *Cell* 59:871–880 (Dec. 1, 1989).
Wilson et al., *Cell*, 74:115–125 (Jul. 16, 1993).
Zhurkin et al., *J. Mol. Biol.*, vol. 239, 181–200 (1994).

*Primary Examiner*—B J Foreman
*Assistant Examiner*—Cynthia Wilder
(74) *Attorney, Agent, or Firm*—Caesar, Rivise, Bernstein, Cohen & Pokotilow, Ltd.

(57) ABSTRACT

Triplex complexes contain a single-stranded probe bound to a double-stranded nucleic acid target, in which the probe includes a heteropolymeric nucleic acid or a heteropolymeric nucleic acid analog. All base triplets of the complex are members selected from the group consisting of A-T-A, T-A-T, U-A-T, T-A-U, A-U-A, U-A-U, G-C-G and C-G-C. A cation-facilitated assay includes detecting the presence of such triplex complexes to determine the degree of complementarity between the probe and target sequence. The assay preferably detects a change in fluorescent intensity of a label as a function of binding affinity between the probe and target. The label can be covalently tethered to the probe or to the target, or can be an intercalating fluorophore in the reaction medium.

16 Claims, 16 Drawing Sheets

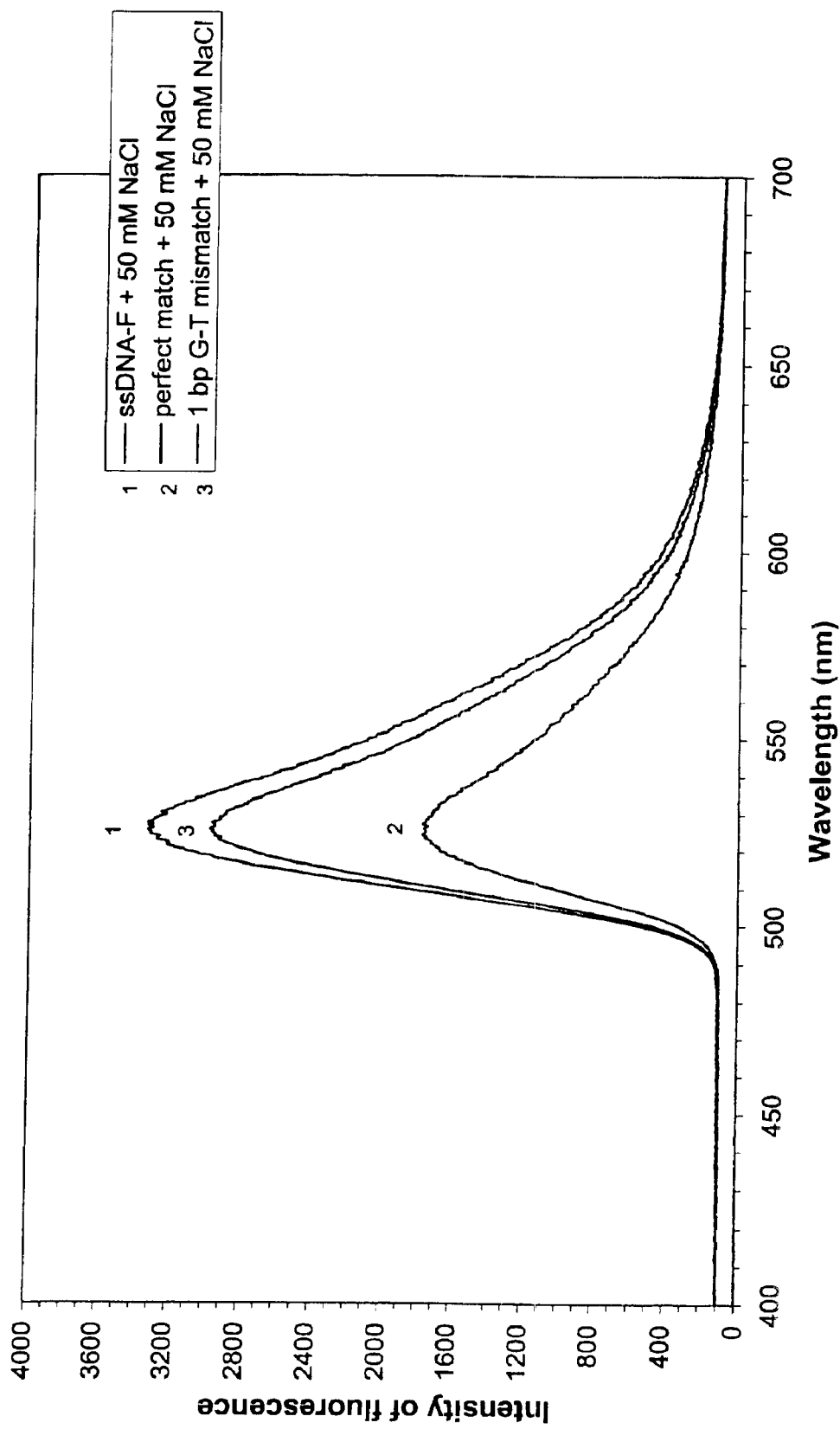
FIG. 1A. Mix of 15-mer ssDNA-F probe (4 pmole) (33% GC) and 50-mer dsDNA (0.4 pmole) in the presence of 50 mM NaCl (after 1 hr)

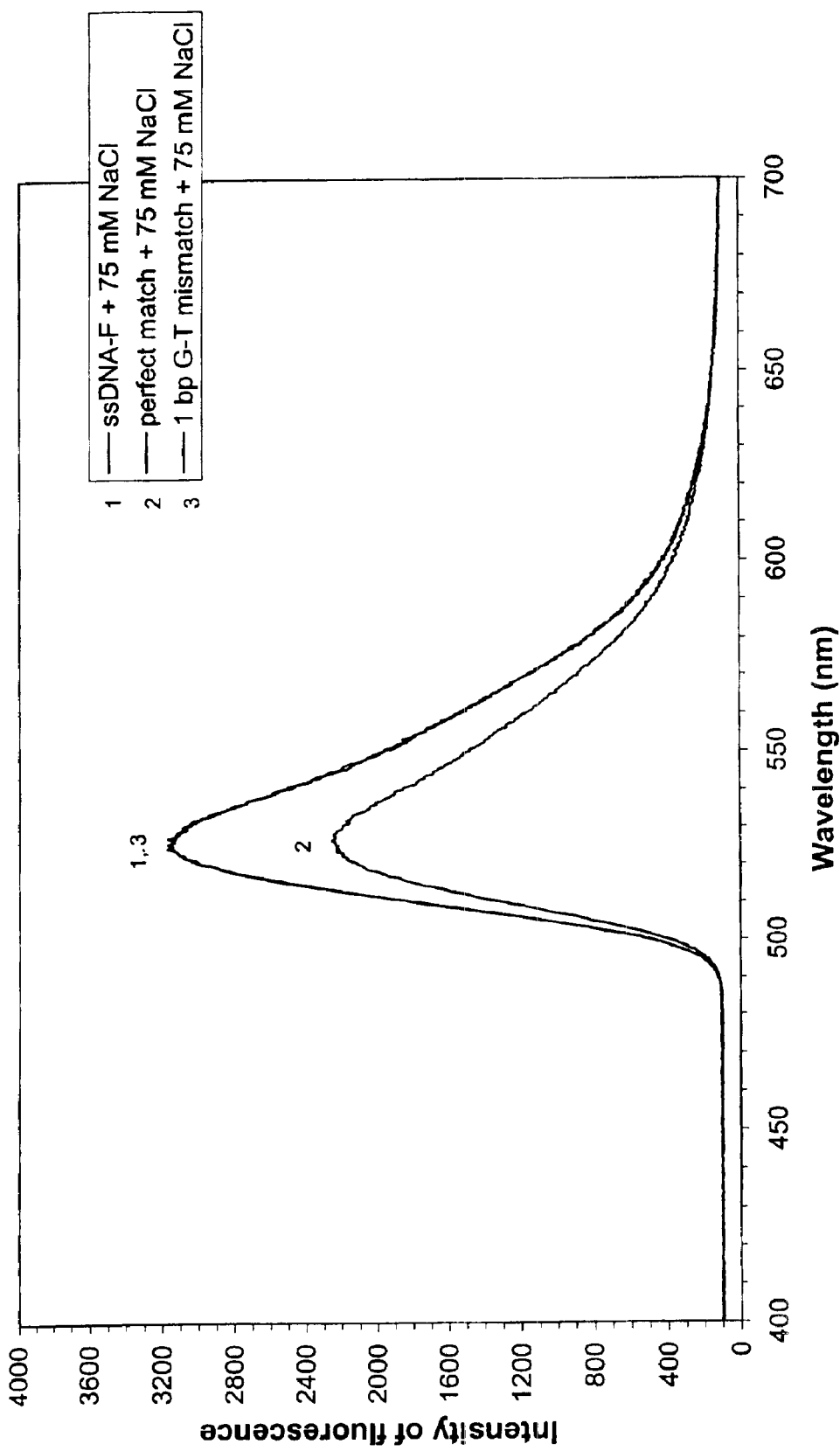
FIG. 1B. Mix of 15-mer ssDNA-F probe (4 pmole) (33% GC) and 50-mer dsDNA (0.4 pmole) in the presence of 75 mM NaCl (after 1 hr)

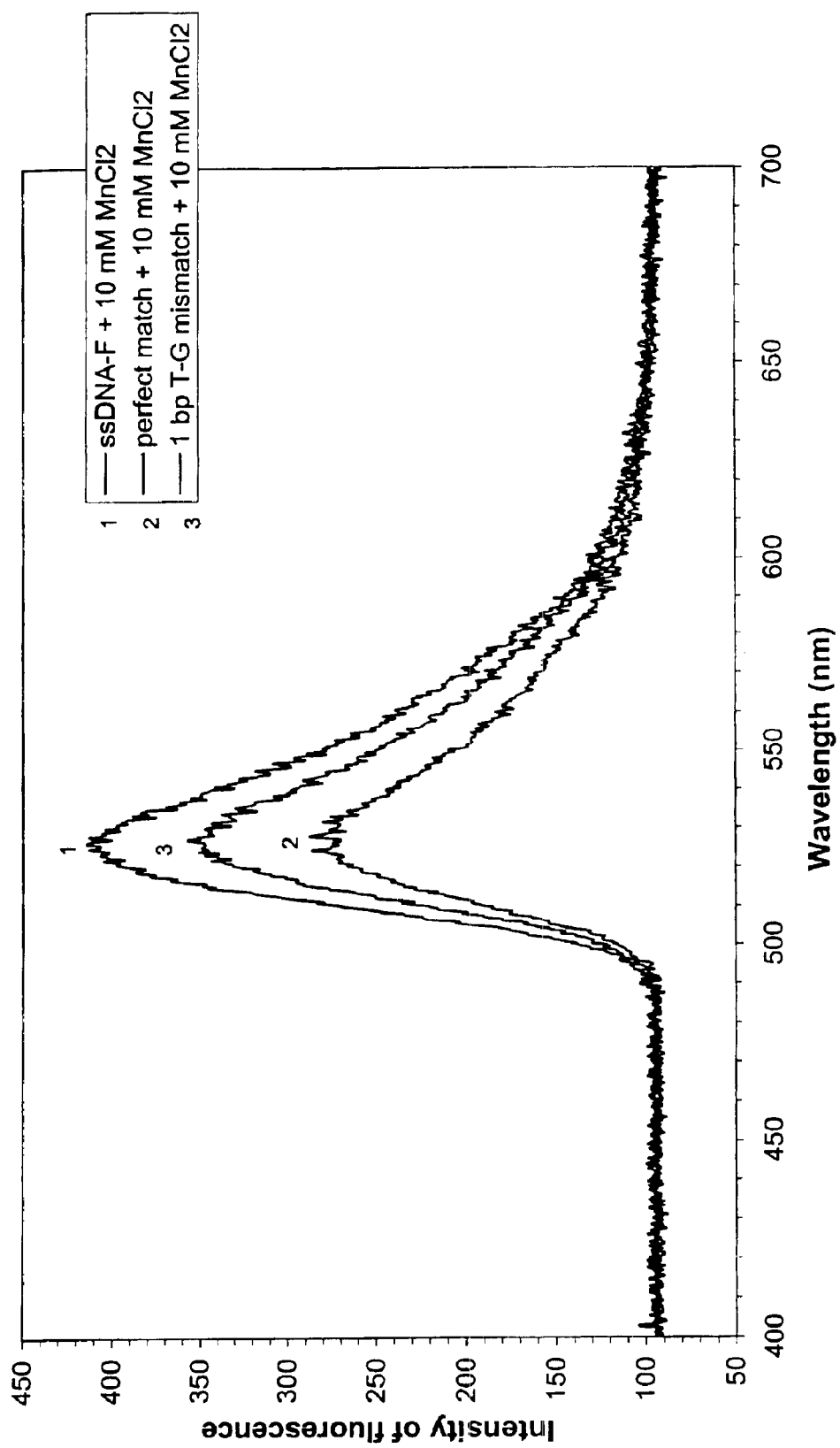
FIG. 2A. Mix of 15-mer ssDNA-F probe (4 pmole) (53% GC) and 50-mer dsDNA (0.4 pmole) in the presence of divalent cations (after 1 hr)

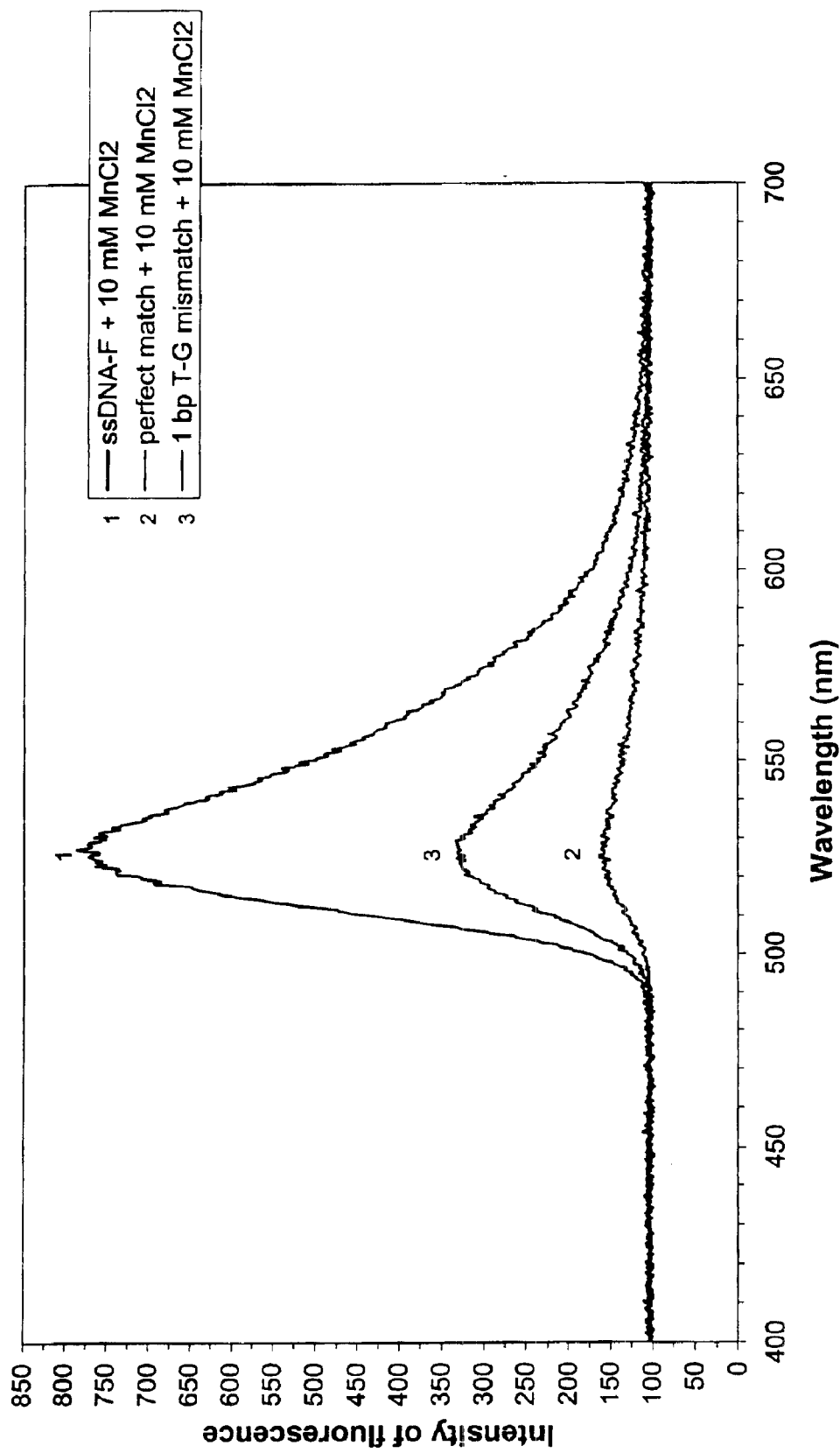
FIG. 2B. Mix of 15-mer ssDNA-F probe (4 pmole) (53% GC) and 50-mer dsDNA (0.4 pmole) in the presence of divalent cations (after 22 hr)

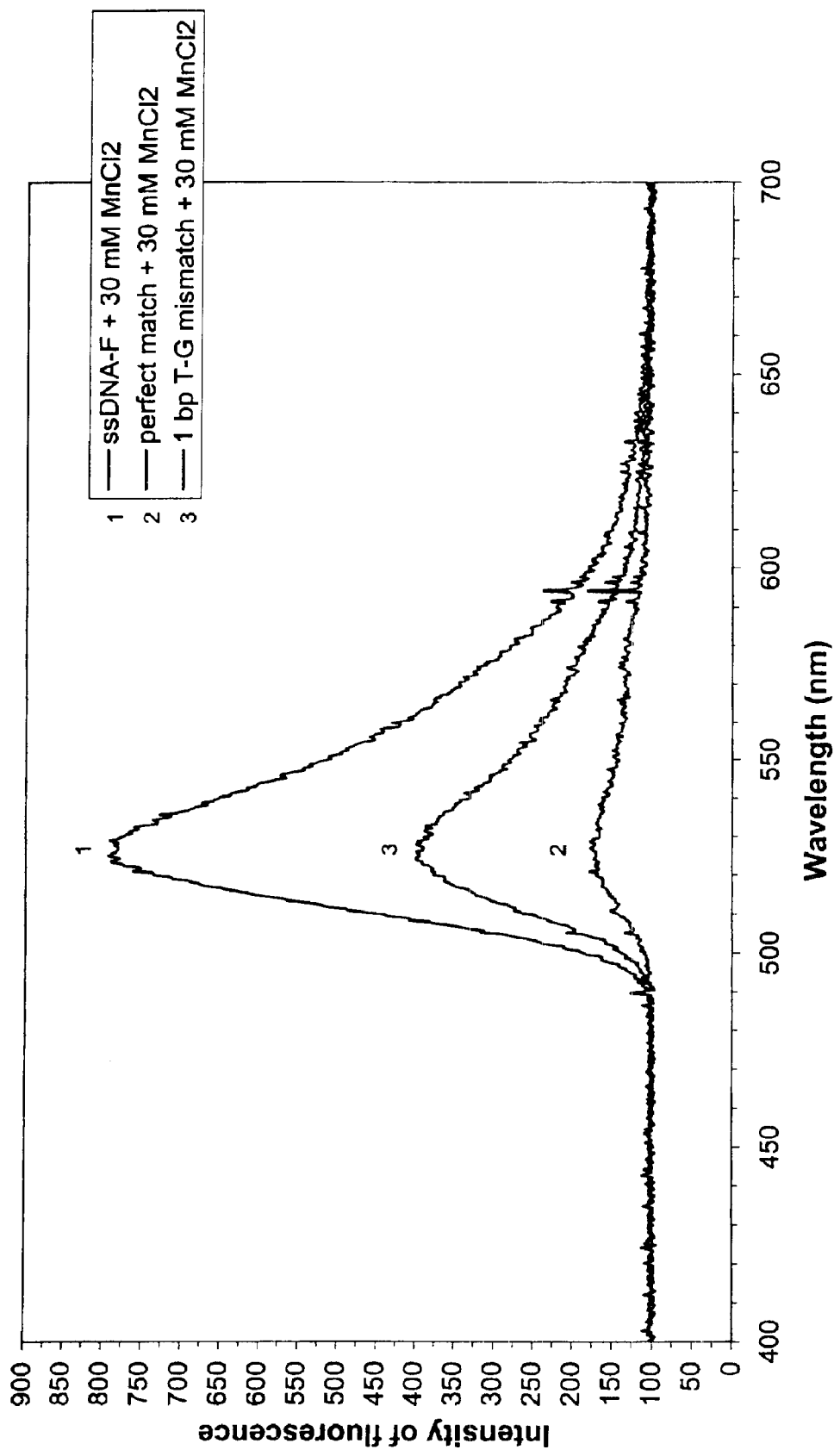

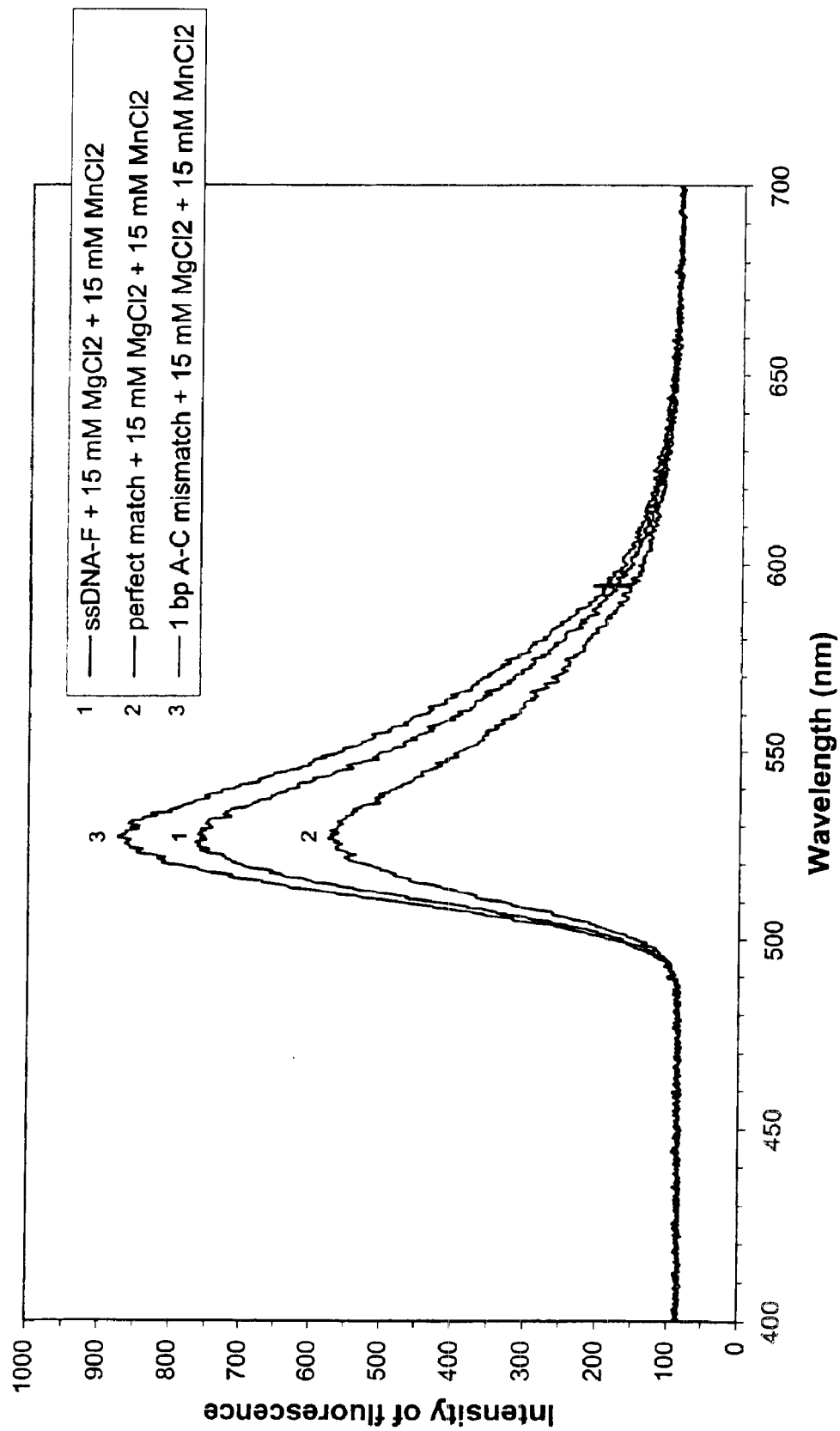
FIG. 3A. Mix of 15-mer ssDNA-F probe (4 pmole) (73%GC) and 50-mer dsDNA (0.4 pmole) in the presence of divalent cations (after 1 hr)

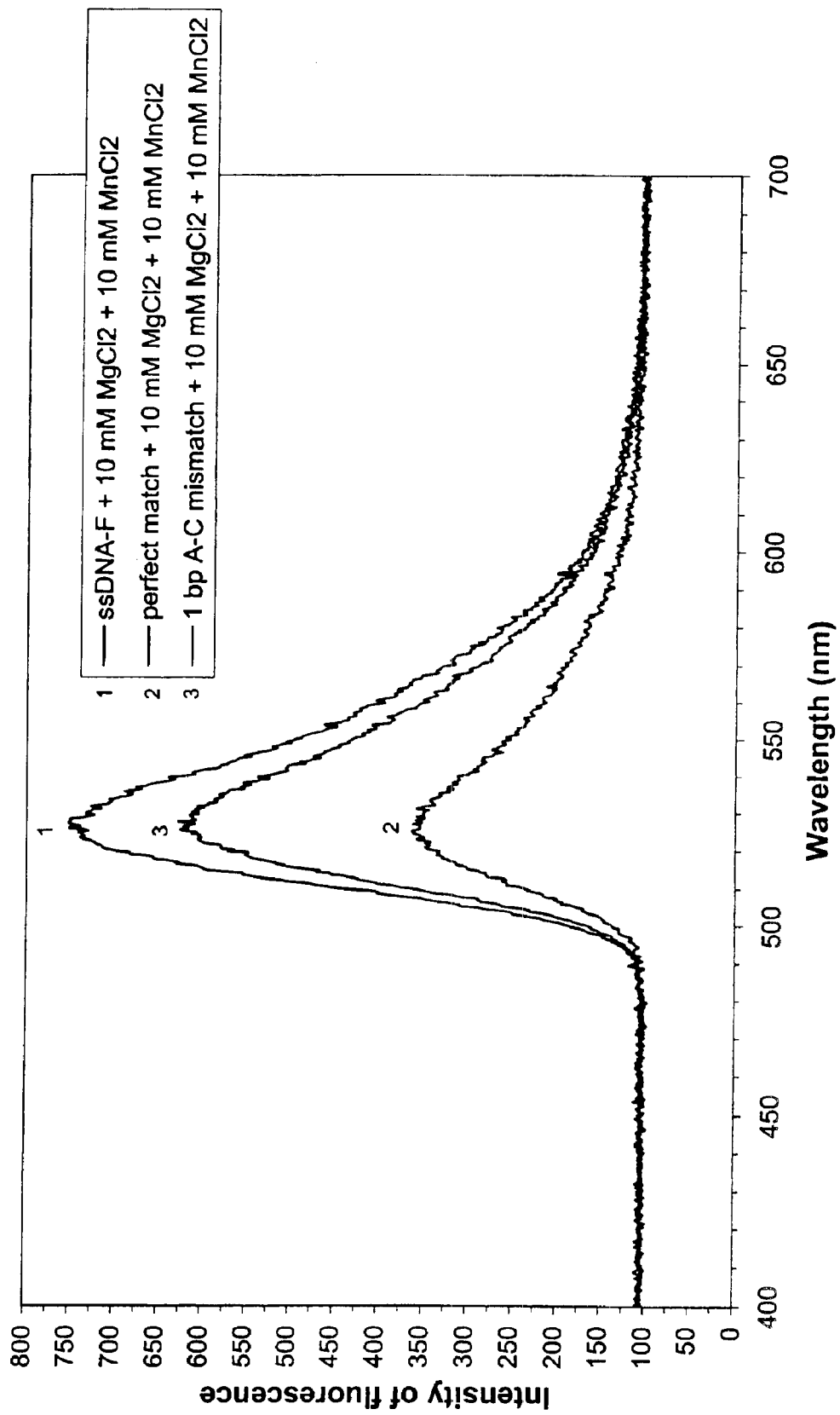
FIG. 3B. Mix of 15-mer ssDNA-F probe (4 pmole) (73% GC) and 50-mer dsDNA (0.4 pmole) in the presence of divalent cations (after 22hr)

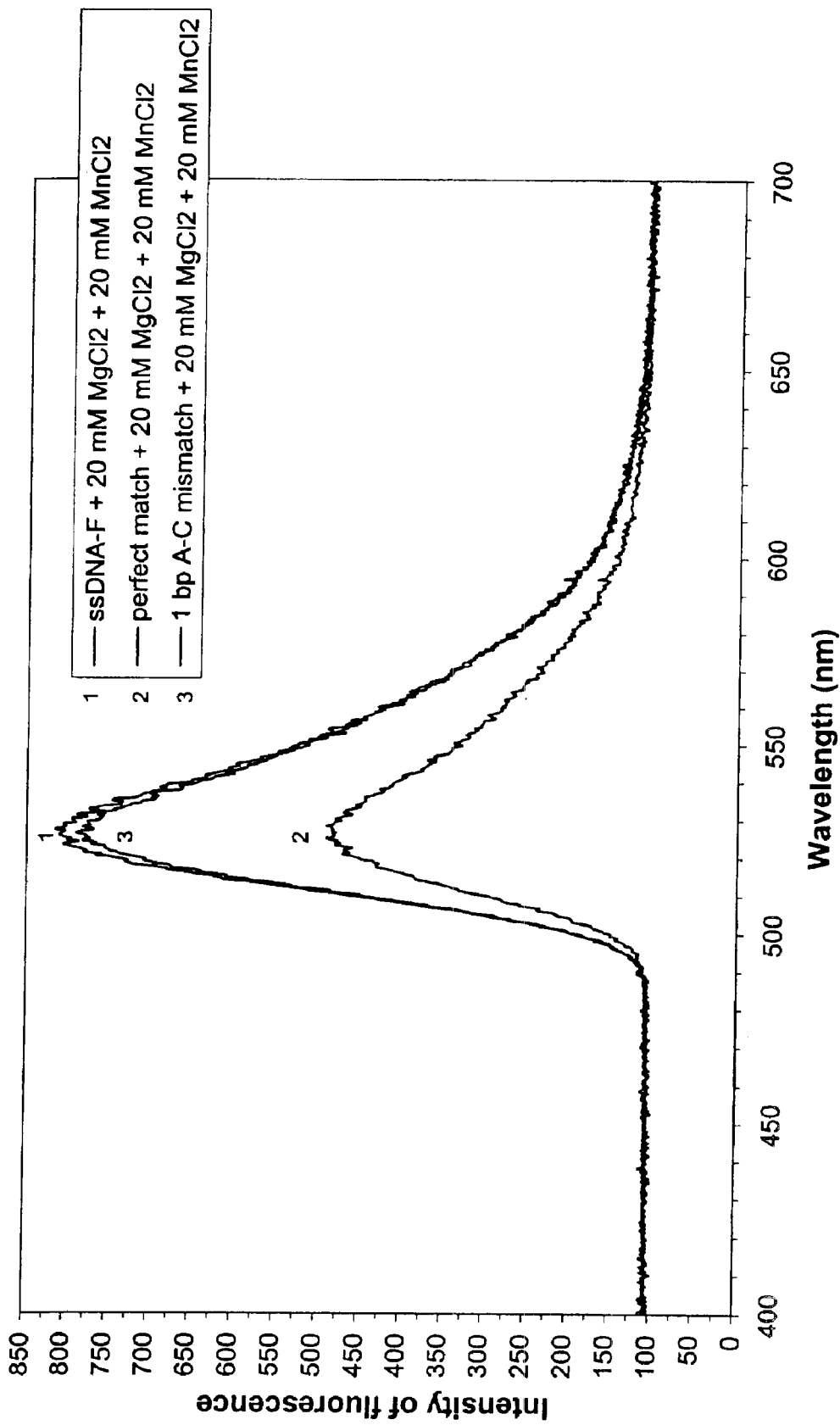
FIG. 3C. Mix of 15-mer ssDNA-F probe (4 pmole) (73% GC) and 50-mer dsDNA (0.4 pmole) in the presence of divalent cations (after 1 hr)

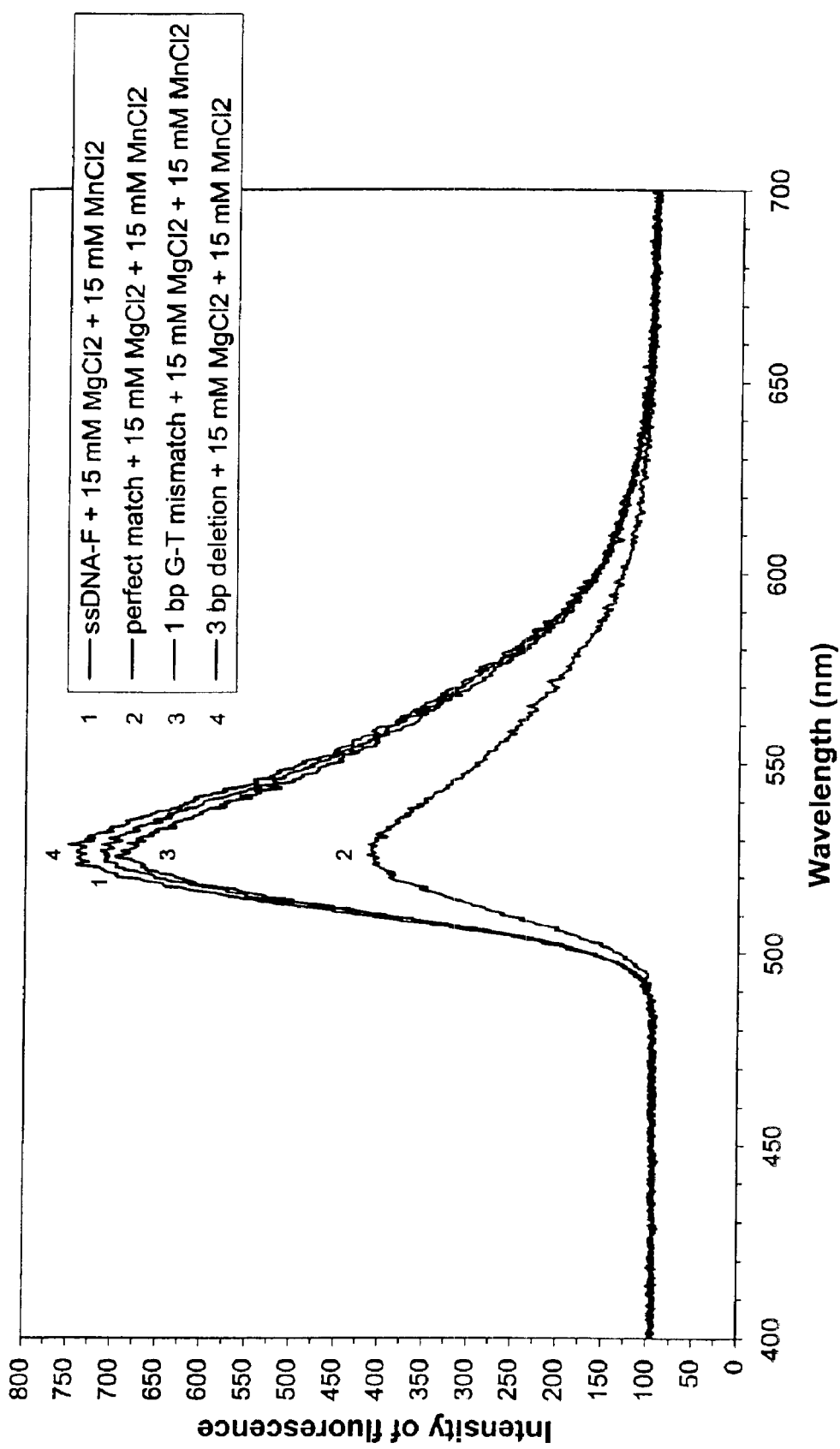
FIG. 4A. Mix of 15-mer ssDNA-F probe (4 pmole) (33% GC) and 50-mer dsDNA (0.4 pmole) in the presence of divalent cations (after 1 hr)

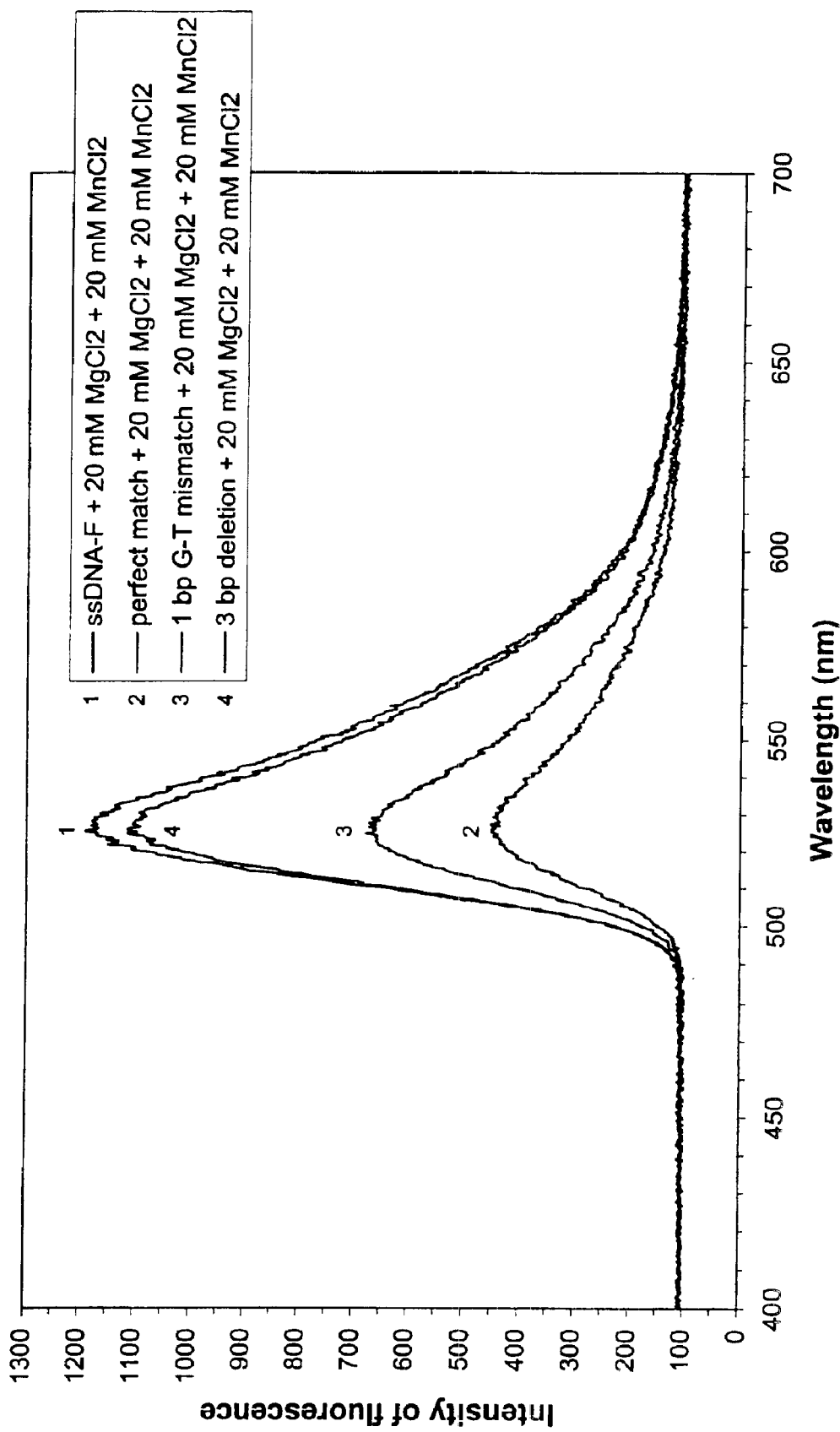
FIG. 4B. Mix of 15-mer ssDNA-F probe (4 pmole) (33% GC) and 50-mer dsDNA (0.4 pmole) in the presence of divalent cations (after 1 hr)

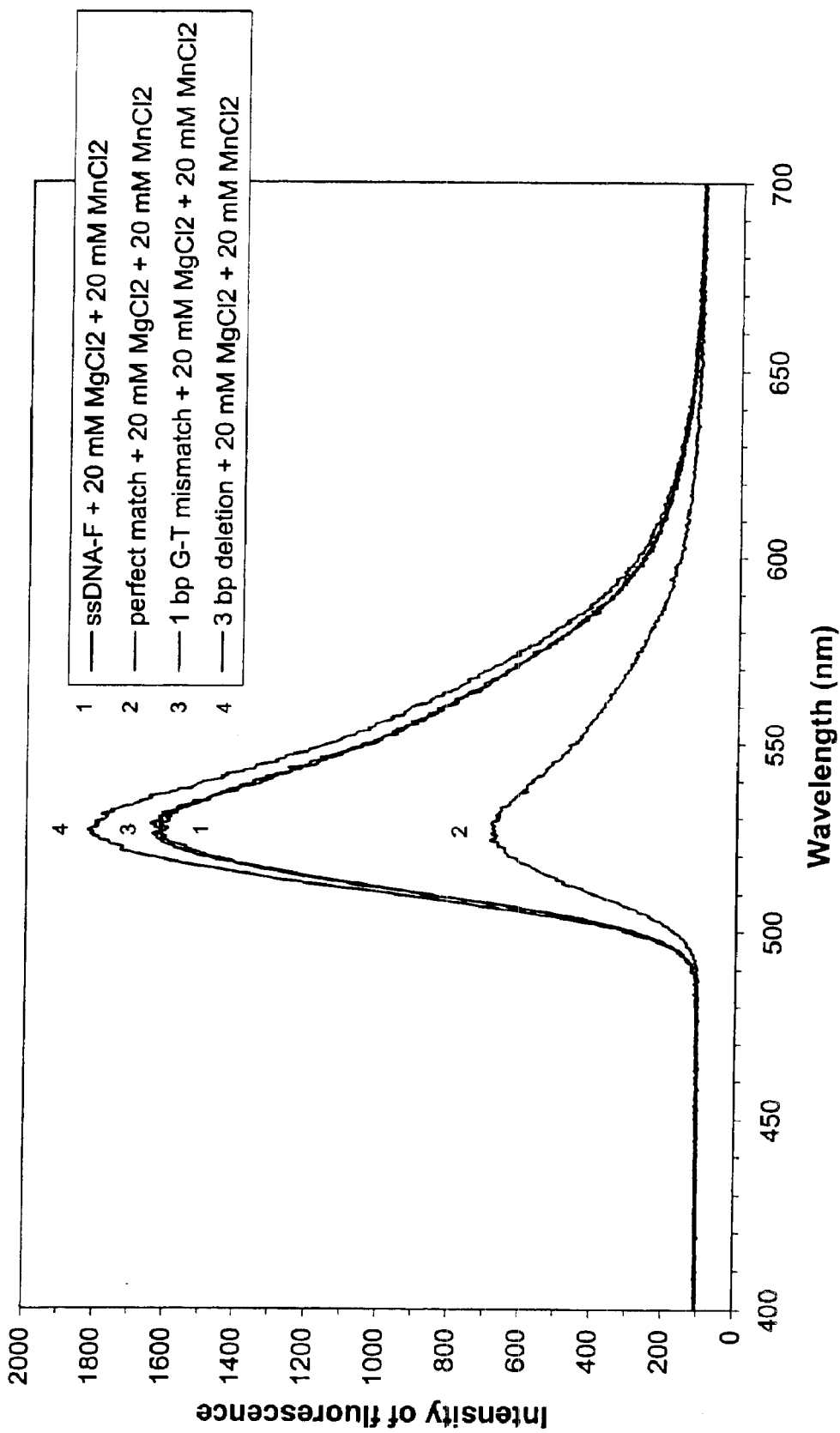
FIG. 4C. Mix of 15-mer ssDNA-F probe (4 pmole) (33% GC) and 50-mer dsDNA (0.4 pmole) in the presence of divalent cations (after 22 hr).

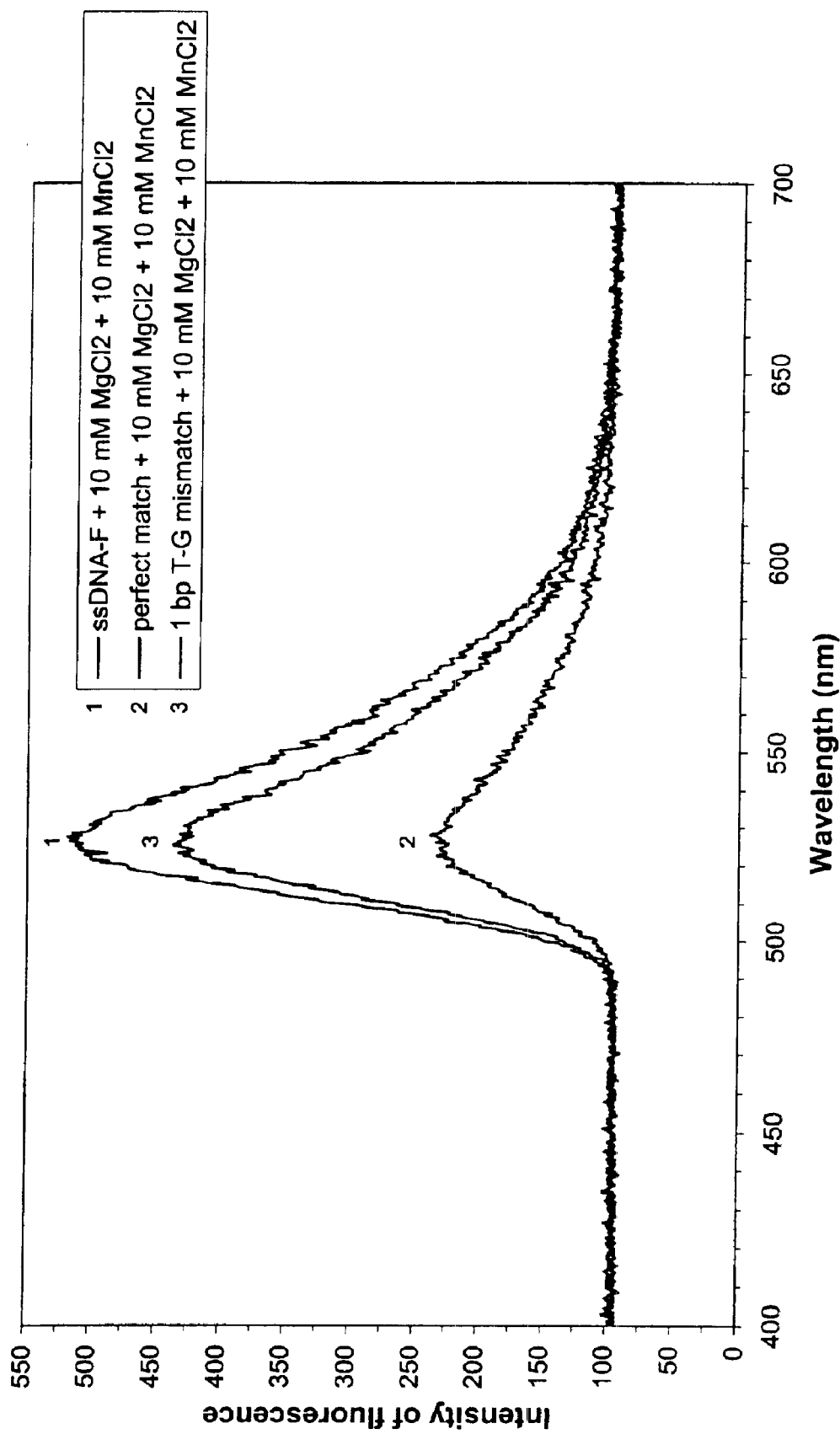
FIG. 5A. Mix of 15-mer ssDNA-F probe (4 pmole) (53% GC) and 50-mer dsDNA (0.4 pmole) in the presence of divalent cations (after 1 hr)

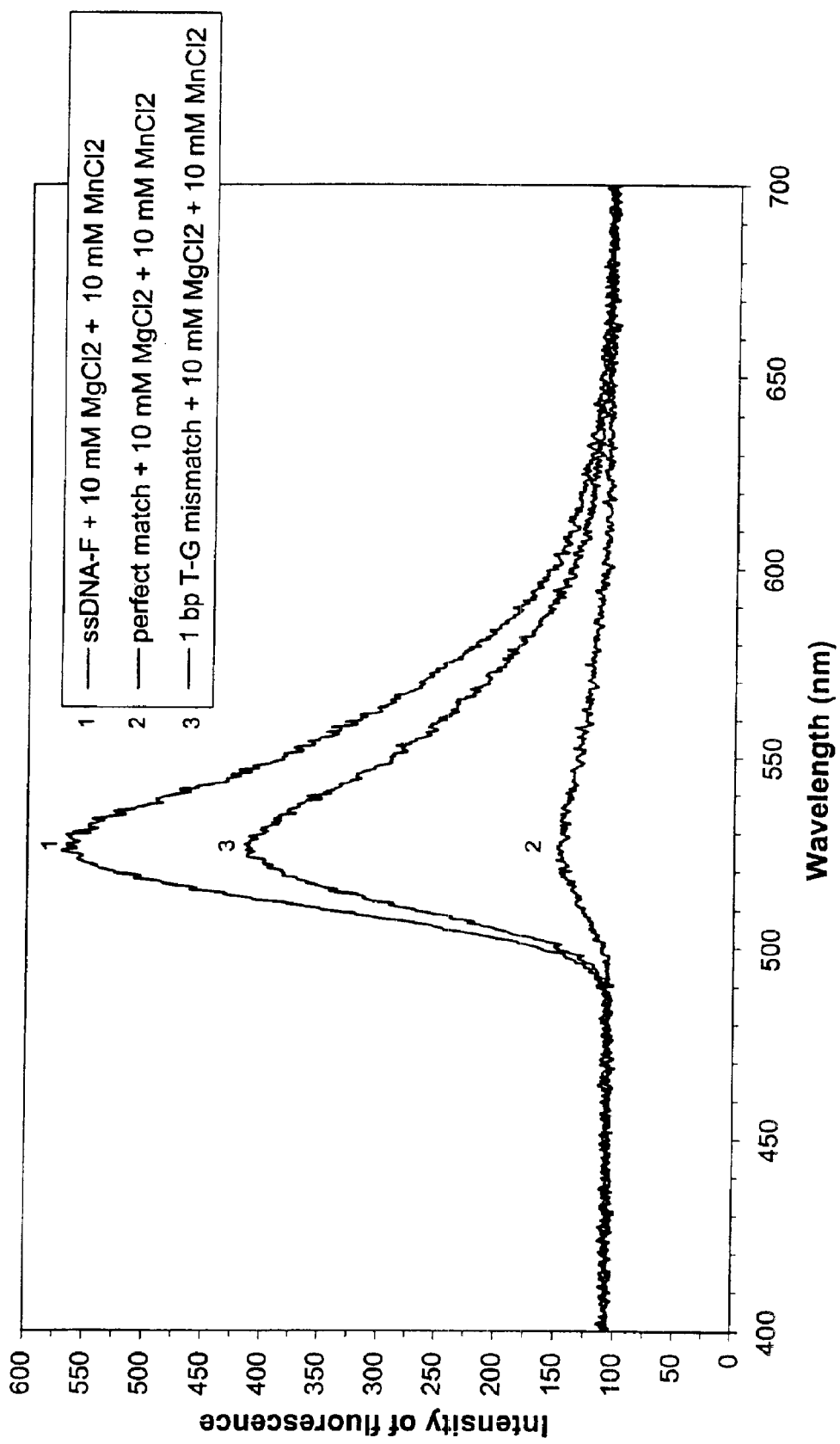
FIG. 5B. Mix of 15-mer ssDNA-F probe (4 pmole) (53% GC) and 50-mer dsDNA (0.4 pmole) in the presence of divalent cations (after 22 hr)

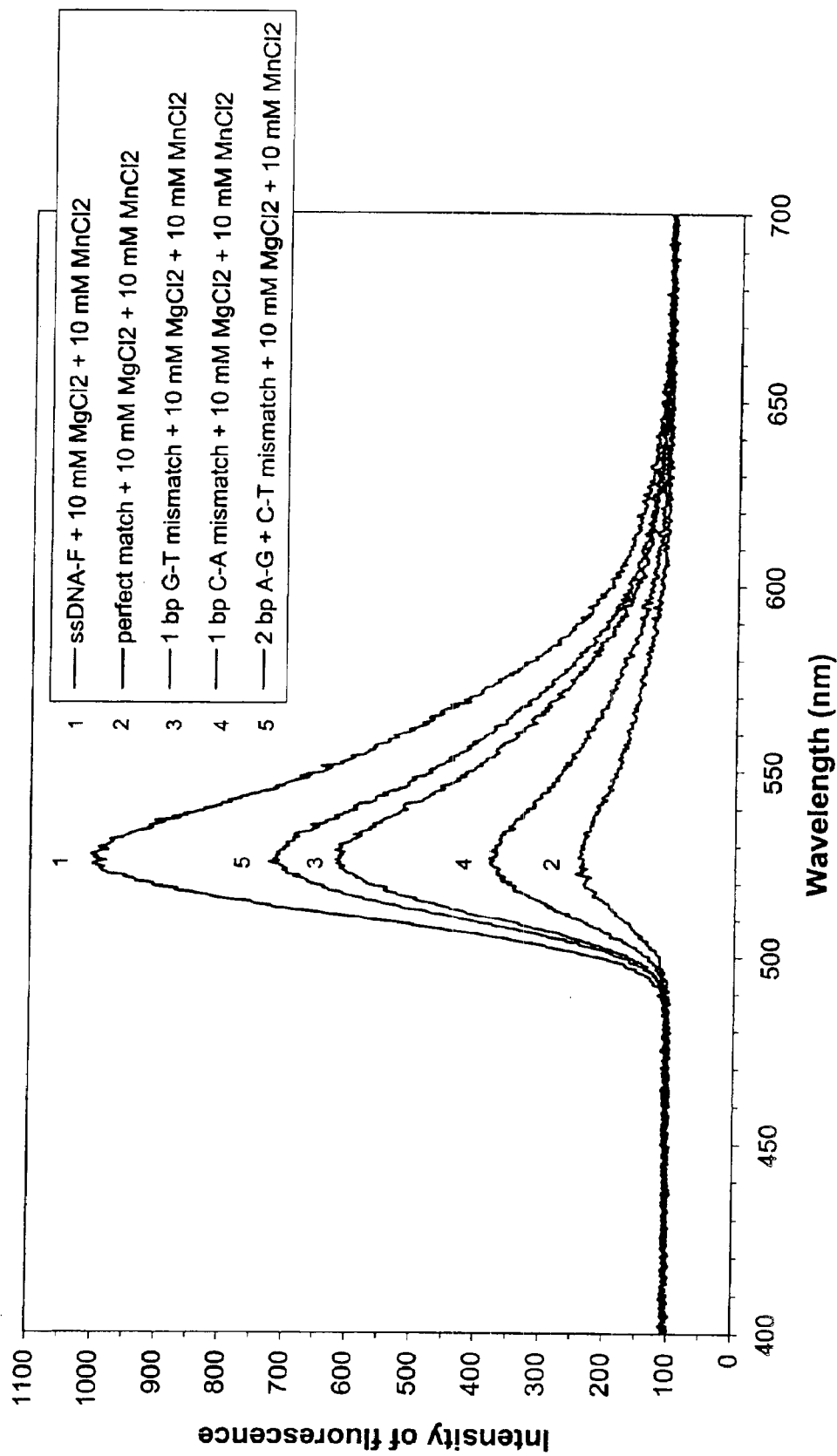
FIG. 5C. Mix of 15-mer ssDNA-F probe (4 pmole) (53% GC) and 50-mer dsDNA (0.4 pmole) in the presence of divalent cations (after 22 hr)

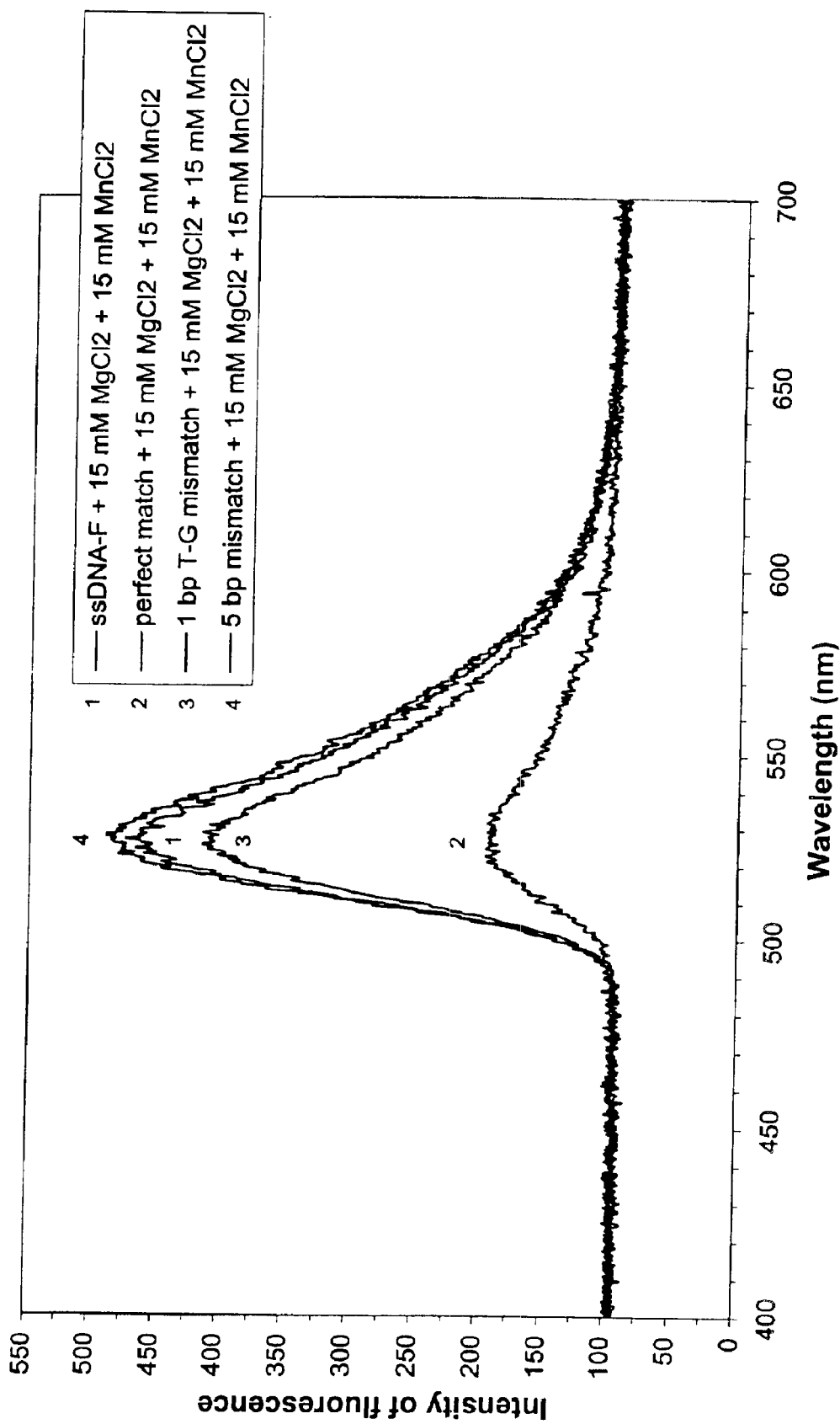
FIG. 5D. Mix of 15-mer ssDNA-F probe (4 pmole) (53% GC) and 50-mer dsDNA (0.4 pmole) in the presence of divalent cations (after 1 hr)

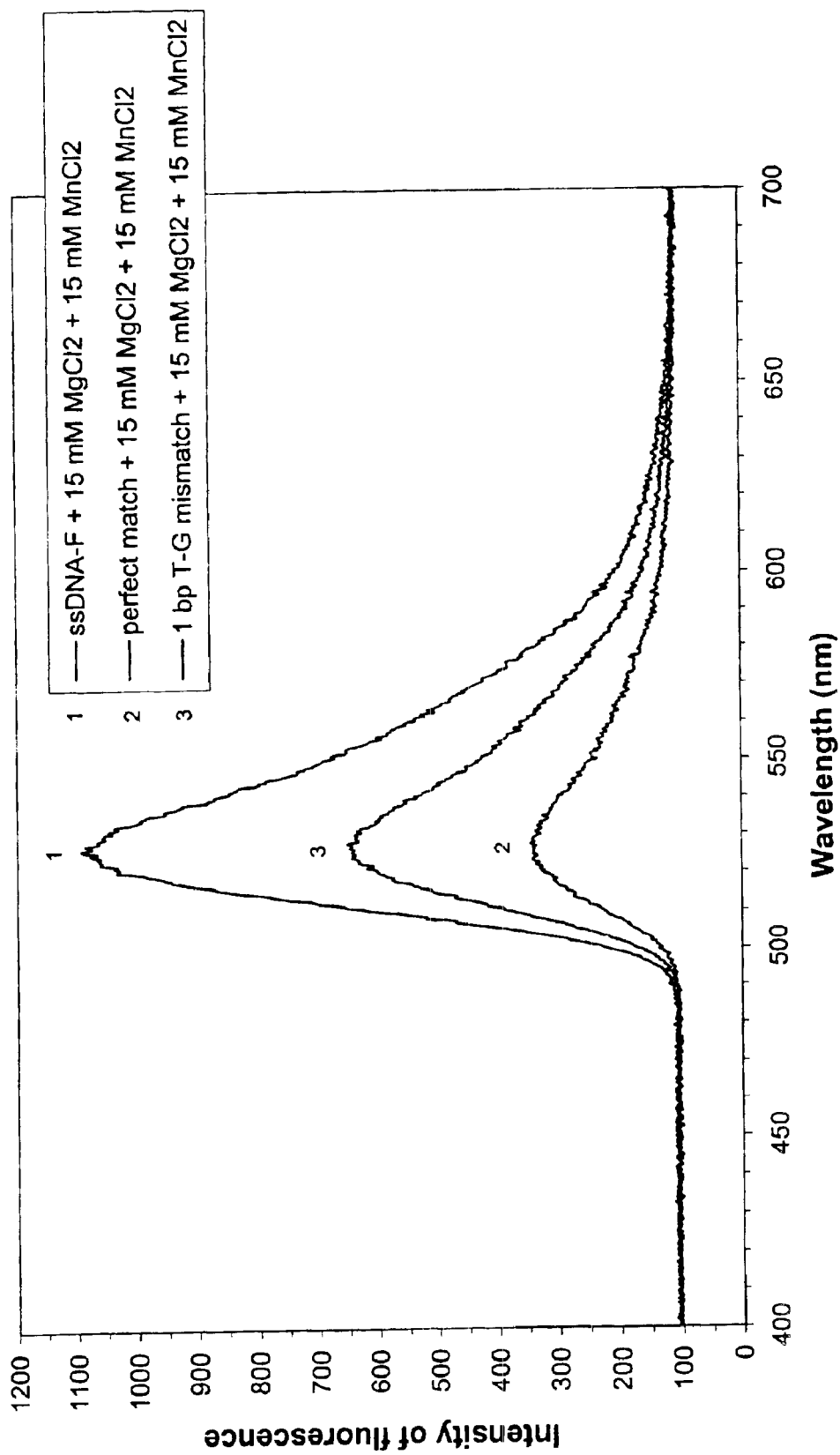
FIG. 5E. Mix of 15-mer ssDNA-F probe (4 pmole) (53% GC) and 50-mer dsDNA (0.4 pmole) in the presence of divalent cations (after 22 hr)

SEQUENCE LISTING

```
<160> NUMBER OF SEQ ID NOS: 15

<210> SEQ ID NO 1
<211> LENGTH: 50
<212> TYPE: DNA
<213> ORGANISM: Artificial Sequence
<220> FEATURE:
<223> OTHER INFORMATION: Description of Artificial Sequence:  derived
      from exon 10 of the human cystic fibrosis gene

<400> SEQUENCE: 1
tggcaccatt aaagaaaata tcatctttgg tgtttcctat gatgaatata              50

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 2
tggcaccatt aaagaaaata tcgtctttgg tgtttcctat gatgaatata              50

<210> SEQ ID NO 3
<211> LENGTH: 47
<212> TYPE: DNA
<213> ORGANISM: Artificial Sequence
<220> FEATURE:
<223> OTHER INFORMATION: Description of Artificial Sequence:  derived
      from exon 10 of the human cystic fibrosis gene

<400> SEQUENCE: 3
tggcaccatt aaagaaaata tcattggtgt ttcctatgat gaatata                 47

<210> SEQ ID NO 4
<211> LENGTH: 15
<212> TYPE: DNA
<213> ORGANISM: Artificial Sequence
<220> FEATURE:
<223> OTHER INFORMATION: Description of Artificial Sequence: ssDNA probe

<400> SEQUENCE: 4
caccaaagat gatat                                                    15

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence:  derived
      from exon 10 of the human cystic fibrosis gene

<400> SEQUENCE: 5
gagcaccatg acagacactg tcatctctgg tgtgtcctac gatgactctg              50
```

```
<210> SEQ ID NO 6
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 6
gagcaccatg acagacactg tcatctttgg tgtgtcctac gatgactctg          50

<210> SEQ ID NO 7
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 7
gagcaccatg acagacactg tcgtctctgg tgtgtcctac gatgactctg          50

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 8
gagcaccatg acagacactg tcttctctgg tgtgtcctac gatgactctg          50

<210> SEQ ID NO 9
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 9
gagcaccatg acagacactg tcatccctgg tgtgtcctac gatgactctg          50

<210> SEQ ID NO 10
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 10
gagcaccatg acagacactg tcatcgctgg tgtgtcctac gatgactctg          50

<210> SEQ ID NO 11
<211> LENGTH: 50
<212> TYPE: DNA
<213> ORGANISM: Artificial Sequence
<220> FEATURE:
<223> OTHER INFORMATION: Description of Artificial Sequence: derived
      from exon 10 of the human cystic fibrosis gene

<400> SEQUENCE: 11
gagcaccatg acagacactg tactctctgg tgtgtcctac gatgactctg          50
```

-continued

```
<210> SEQ ID NO 12
<211> LENGTH: 50
<212> TYPE: DNA
<213> ORGANISM: Artificial Sequence
<220> FEATURE:
<223> OTHER INFORMATION: Description of Artificial Sequence:  derived
      from exon 10 of the human cystic fibrosis gene

<400> SEQUENCE: 12
gagcaccctc ccaggcacgg tcgtccctgg tgcgacctcc gacgagcgtg              50

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence:  derived
      from exon 10 of the human cystic fibrosis gene

<400> SEQUENCE: 13
gagcaccctc ccaggcacgg tcatccctgg tgcgacctcc gacgagcgtg              50

<210> SEQ ID NO 14
<211> LENGTH: 15
<212> TYPE: DNA
<213> ORGANISM: Artificial Sequence
<220> FEATURE:
<223> OTHER INFORMATION: Description of Artificial Sequence: ssDNA probe

<400> SEQUENCE: 14
caccagagat gacag                                                   15

<210> SEQ ID NO 15
<211> LENGTH: 15
<212> TYPE: DNA
<213> ORGANISM: Artificial Sequence
<220> FEATURE:
<223> OTHER INFORMATION: Description of Artificial Sequence:  ssDNA
      probe

<400> SEQUENCE: 15
caccagggac gaccg                                                   15
```

HETEROPOLYMERIC TRIPLEXES CONTAINING WATSON-CRICK TRIPLETS

CROSS-REFERENCE TO RELATED APPLICATIONS

This application is a divisional of Ser. No. 09/613,263, filed Jul. 10, 2000, now U.S. Pat. No. 6,420,115, which is continuation-in-part of U.S. patent application Ser. No. 09/468,679, filed Dec. 21, 1999 now U.S. Pat. No. 6,403,313.

BACKGROUND OF THE INVENTION

1. Field of Invention

The invention relates to nucleic acid triplexes, and more particularly to methods of accurately assaying triplex nucleic acid complexes employing fluorescent intensity measurements.

2. Description of Related Art

Fluorescent dyes have been used to detect and quantitate nucleic acids for decades. In their most basic form, fluorescent intensity-based assays have typically comprised contacting a target with a fluorophore-containing probe, removing any unbound probe from bound probe, and detecting fluorescence in the washed sample. Homogeneous assays improve upon such basic assays, in that the former do not require a washing step or the provision of a non-liquid phase support.

For example, U.S. Pat. No. 5,538,848 to Livak et al. and U.S. Pat. No. 4,220,450 to Maggio disclose homogeneous fluorescence-based assays of nucleotide sequences using oligonucleotide probes in solution. However, these patents require the use of a quenching agent in combination with a reporting agent, so as to distinguish between the signals generated by hybridized probes and unhybridized probes. Livak et al. also requires the use of enzymes in its disclosed method. Quenching agents and enzymes add complexity and expense to the methods.

U.S. Pat. No. 5,332,659 to Kidwell discloses a method for detecting nucleotide sequences in solution using probes comprising at least two fluorophore moieties. The fluorophores must be selected to electronically interact with each other when close enough to vary the wavelength dependence of their spectra. Unhybridized probes are much more flexible than probes hybridized to the target sequence, and consequently the two fluorophore moieties on each probe are more likely to be close to each other when the probe is unhybridized than when the probe is hybridized. Thus, a change in emission wavelength correlated with free probe can be monitored as an indication of the amount of free probe in the sample.

U.S. Pat. No. 5,846,729 to Wu et al. also discloses homogeneous fluorescence-based assays for detecting nucleic acid.

In addition to the aforementioned developments which detect fluorescent intensity, some have touted the advantages of fluorescent polarization assays. However, there are significant drawbacks to polarization-based assays. The degree of change in polarization as a function of binding can be unpredictable, and interpretation of data to conform inconsistent data to theoretical expectations can require more effort than is desirable in an analytical method, particularly when the method is to be automated. There are as well constraints arising from the molecular weight of the molecules whose motion is being evaluated in a fluorescent polarization assay.

Conventional assays for nucleic acids have generally been based on a duplex hybridization model, wherein a single-stranded probe specifically binds to a complementary single-stranded target sequence. Triplex hybridization of nucleic acids has been previously identified in the art; however, hybridization among three strands was largely believed to be confined to very limited species of nucleic acids (e.g., polypurine or polypyrimidine sequences). See, e.g., Floris et al., "Effect of cations on purine-purine-pyrimidine triple helix formation in mixed-valence salt solutions," 260 Eur. J. Biochem. 801–809 (1999). Moreover, such triplex formation or hybridization was based on Hoogsteen binding between limited varieties of adjacent nucleobases, rather than Watson-Crick base pairing. See, e.g., Floris et al. and U.S. Pat. No. 5,874,555 to Dervan et al.

Despite the foregoing developments, a need has continued to exist in the art for additional simple, highly sensitive, effective and rapid methods for analyzing interaction between nucleic acids and/or nucleic acid analogs.

All references cited herein are incorporated herein by reference in their entireties.

SUMMARY OF THE INVENTION

The invention provides triplex complexes comprising a single-stranded probe bound to a double-stranded nucleic acid target, wherein the probe comprises a heteropolymeric nucleic acid or a heteropolymeric nucleic acid analog, and all base triplets of the complex are members selected from the group consisting of A-T-A, T-A-T, U-A-T, T-A-U, A-U-A, U-A-U, G-C-G and C-G-C.

Also provided is a method for assaying binding, said method comprising:

providing a double-stranded nucleic acid comprising a target sequence, wherein said target sequence contains at least one purine base and at least one pyrimidine base;

providing a probe comprising a nucleic acid sequence or a nucleic acid analog sequence;

providing a cation;

adding said probe, said target sequence and said cation to a medium to provide a test sample containing a triplex complex comprising said probe bound to said target sequence, wherein all base triplets of said complex are members selected from the group consisting of A-T-A, T-A-T, U-A-T, T-A-U, A-U-A, U-A-U, G-C-G and C-G-C;

irradiating said test sample with exciting radiation to cause test sample to emit fluorescent radiation;

detecting an intensity of said fluorescent radiation, wherein said intensity is correlated with a binding affinity between said probe and said target sequence; and determining from said intensity an extent of matching between said probe and said target sequence.

BRIEF DESCRIPTION OF THE DRAWINGS

The invention will be described in conjunction with the following drawings in which like reference numerals designate like elements and wherein:

FIGS. 1A, 1B, 2A, 2B, 2C, 3A, 3B, 3C, 4A, 4B, 4C, 5A, 5B, 5C, 5D and 5E are composite graphs of fluorescent intensity plotted as a function of wavelength for each sample analyzed.

DETAILED DESCRIPTION OF PREFERRED EMBODIMENTS

The invention provides triplex complexes comprising a single-stranded probe bound to a double-stranded nucleic acid target, wherein the probe comprises a heteropolymeric nucleic acid or a heteropolymeric nucleic acid analog, and all base triplets of the complex are members selected from the group consisting of A-T-A, T-A-T, U-A-T, T-A-U, A-U-A, U-A-U, G-C-G and C-G-C.

Unlike certain Hoogsteen triplexes disclosed by the prior art, the triplexes of the invention are stable at pH values greater than 7.6. Moreover, the inventive triplexes do not require the presence of homopyrimidine sequences or homopurine sequences, as in certain prior art triplexes. For example, the target sequence can contain 25% to 75% purine bases and 75% to 25% pyrimidine bases in any order.

Preferably the single-stranded nucleic acid or nucleic acid analog of the triplex is 5 to 30 bases long and the double-stranded nucleic acid target is 8 to $3.3 \times 10^9$ base pairs long.

Triplex formation according to the invention is suitable for a variety of uses. For example, probes covalently bound to a double-stranded nucleic acid cleaving agent can be used to specifically cleave target sequences of double-stranded nucleic acids. Probes covalently bound to a chemotherapeutic agent can be used to specifically treat target sequences of double-stranded nucleic acids. In preferred embodiments, the invention provides a rapid, sensitive, environmentally friendly, and safe method for assaying binding between a double-stranded target and a single-stranded probe, wherein the target comprises a nucleic acid sequence or a nucleic acid analog sequence and the probe comprises a nucleic acid sequence or a nucleic acid analog sequence.

Unlike certain prior art assays, the invention not only detects the presence of specific probe-target binding, but also provides qualitative and quantitative information regarding the nature of interaction between a probe and target. Thus, the invention enables the practitioner to distinguish among a perfect match, a one base pair mismatch, a two base pair mismatch, a three base pair mismatch, a one base pair deletion, a two base pair deletion and a three base pair deletion arising between a base sequence in the probe and in a strand of the double-stranded target.

Embodiments of the invention comprise calibrating the measured signal (e.g., fluorescent intensity) for a first probe-target mixture against the same type of signal exhibited by other probes combined with the same target, wherein each of the other probes differs from the first probe by at least one base.

A calibration curve can be generated, wherein the magnitude of the measured signal (e.g., fluorescent intensity) is a function of the binding affinity between the target and probe. As the binding affinity between the target and a plurality of different probes varies with the number of mismatched bases, the nature of the mismatch(es) (A-G vs. A-C vs. T-G vs. T-C, etc.), the location of the mismatch(es) within the triplex, etc., the assay of the invention can be used to sequence the target.

In embodiments, the signal measured can be the fluorescent intensity of a fluorophore included in the test sample. In such embodiments, the binding affinity between the probe and target can be directly or inversely correlated with the intensity, depending on whether the fluorophore signals hybridization through signal quenching or signal amplification. Under selected conditions, the fluorescent intensity generated by intercalating agents can be directly correlated with probe-target binding affinity, whereas the intensity of preferred embodiments employing a non-intercalating fluorophore covalently bound to the probe can be inversely correlated with probe-target binding affinity. The fluorescent intensity decreases for non-intercalating fluorophores as the extent of matching between the probe and target increases, preferably over a range inclusive of 0–2 mismatches and/or deletions, more preferably over a range inclusive of 0–3 mismatches and/or deletions.

The invention enables quantifying the binding affinity between probe and target. Such information can be valuable for a variety of uses, including designing antisense drugs with optimized binding characteristics.

Unlike prior art methods, the assay of the invention is preferably homogeneous. The assay can be conducted without separating the probe-target complex from the free probe and target prior to detecting the magnitude of the measured signal. The assay does not require a gel separation step, thereby allowing a great increase in testing throughput. Quantitative analyses are simple and accurate. Consequently the binding assay saves a lot of time and expense, and can be easily automated. Furthermore, it enables binding variables such as buffer, pH, ionic concentration, temperature, incubation time, relative concentrations of probe and target sequences, intercalator concentration, length of target sequences, length of probe sequences, and possible cofactor requirements to be rapidly determined.

The assay can be conducted in, e.g., a solution within a well, on an impermeable surface or on a biochip.

Moreover, the inventive assay is preferably conducted without providing a signal quenching agent on the target or on the probe.

Although the inventors have previously disclosed the advantages of fluorescent intensity assays for hybridization (see, e.g., U.S. patent application Ser. No. 09/224,505, filed Dec. 31, 1998), assays according to the present invention specifically detect triplexes of the probe and the double-stranded target, thus obviating the need to denature the target. While nucleic acid (and nucleic acid analog) probes have been known to form triplexes with certain limited classes of targets (see, e.g., Floris et al., supra, Dervan et al., supra, Egholm et al., 365 Nature 566 (1993), and Tomac et al., 118 J. Am. Chem. Soc. 5544 (1996)), it is surprising that the inventors have been able to specifically assay triplexes formed between single-stranded nucleic acid (e.g., ssDNA and RNA) probes and double-stranded nucleic acid (e.g., dsDNA) targets, wherein the interaction between the probes and targets is based on Watson-Crick base pairing (at least in the sense that A binds to T (or U, in the case of RNA) and G binds to C), rather than the very limited Hoogsteen model of triplex hybridization of, e.g., Dervan et al. The term "Watson-Crick triplex," which is employed herein, is intended to crystallize these differences by limiting the nature of base pairing between the single-stranded probe and the double-stranded target to A-T-A, T-A-T, U-A-T, T-A-U, A-U-A, U-A-U, G-C-G and/or C-G-C (including $C^+$-G-C, and/or any other ionized species of base). These three-member groups are hereinafter denoted Watson-Crick base triplets and the resulting structures denoted Watson-Crick triplexes.

Suitable probes for use in the inventive assay include, e.g., ssDNA, RNA, PNA and other nucleic acid analogs having uncharged or partially-charged backbones. Probe sequences having any length from 8 to 20 bases are preferred since this is the range within which the smallest unique DNA sequences of prokaryotes and eukaryotes are found. Probes of 12 to 18 bases are particularly preferred since this is the length of the smallest unique sequences in the human genome. In embodiments, probes of 5 to 30 bases are most preferred. However, a plurality of shorter probes can be used to detect a nucleotide sequence having a plurality of nonunique target sequences therein, which combine to uniquely identify the nucleotide sequence. The length of the probe can be selected to match the length of the target.

In parent U.S. application Ser. No. 09/468,679, the inventors disclosed the surprising development that they were able to specifically assay a wide-variety of triplexes formed in a Watson-Crick base-pair dependent manner between single-stranded nucleic acid (e.g., ssDNA, RNA, ssPNA and other analogs of DNA or RNA) probes and double-stranded nucleic acid (e.g., dsDNA) targets. The inventors disclosed that triplex formation and/or stabilization is enhanced by the presence of an intercalating agent in the sample being tested.

The instant disclosure expands upon the earlier one by disclosing that Watson-Crick triplex formation and/or stabilization is enhanced by the presence of cations in the sample being tested. Suitable cations include, e.g., monovalent cations, such as $Na^+$ (preferably at a concentration of 50 mM to 125 mM), $K^+$, and other alkali metal ions; divalent cations, such as alkaline earth metal ions (e.g., $Mg^{+2}$ and $Ca^{+2}$) and divalent transition metal ions (e.g., $Mn^{+2}$, $Ni^{+2}$, $Cd^{+2}$, $Co^{+2}$ and $Zn^{+2}$); and cations having a positive charge of at least three, such as $Co(NH_3)_6^{+3}$, trivalent spermidine and tetravalent spermine. $Mn^{+2}$ is preferably provided at a concentration of 10 mM to 30 mM. $Mg^{+2}$ is preferably provided at a concentration of 15 mM to 20 mM. $Ni^{+2}$ is preferably provided at a concentration of about 20 mM. In embodiments, $Mg^{+2}$ and $Mn^{+2}$ are provided in combination at a concentration of 10 mM each, 15 mM each or 20 mM each (i.e., 10–20 mM each).

The amount of cation added to the medium in which the triplex forms depends on a number of factors, including the nature of the cation, the concentration of probe, the concentration of target, the presence of additional cations and the base content of the probe and target. The preferred cation concentrations and mixtures can routinely be discovered experimentally.

The instant invention does not require the use of radioactive probes, which are hazardous, tedious and time-consuming to use, and need to be constantly regenerated. Probes of the invention are preferably safe to use and stable for years. Accordingly, probes can be made or ordered in large quantities and stored.

In embodiments, the probe is labeled with a multi-molecule signaling complex or a redox pair, or with a label that elicits chemiluminescent or electrochemiluminescent properties.

It is preferred that the probe or target (preferably the probe) have a fluorescent label covalently bound thereto. The label is preferably a non-intercalating fluorophore. In such embodiments, the fluorophore is preferably bound to the probe at either end. Preferred fluorescent markers include biotin, rhodamine and fluorescein, and other markers that fluoresce when irradiated with exciting energy.

The excitation wavelength is selected (by routine experimentation and/or conventional knowledge) to correspond to this excitation maximum for the fluorophore being used, and is preferably 200 to 1000 nm. Fluorophores are preferably selected to have an emission wavelength of 200 to 1000 nm. In preferred embodiments, an argon ion laser is used to irradiate the fluorophore with light having a wavelength in a range of 400 to 540 nm, and fluorescent emission is detected in a range of 500 to 750 nm.

The assay of the invention can be performed over a wide variety of temperatures, such as, e.g., from 5 to 85° C. Certain prior art assays require elevated temperatures, adding cost and delay to the assay. On the other hand, the invention can be conducted at room temperature or below (e.g., at a temperature below 25° C.).

The reliability of the invention is independent of guanine and cytosine content in said target. Since G-C base pairs form three hydrogen bonds, while A-T base pairs form only two hydrogen bonds, target and probe sequences with a higher G or C content are more stable, possessing higher melting temperatures. Consequently, base pair mismatches that increase the GC content of the hybridized probe and target region above that present in perfectly matched hybrids may offset the binding weakness associated with a mismatched probe. Triplexes containing every possible base pair mismatch between the probe and the target proved to be more unstable than perfectly matched triplexes, always resulting in lower fluorescent intensities than did perfectly complementary hybrids, when an intercalating fluorophore was used.

The inventive assay is extremely sensitive, thereby obviating the need to conduct PCR amplification of the target. For example, it is possible to assay a test sample having a volume of about 20 microliters, which contains about 10 femtomoles of target and about 10 femtomoles of probe. Embodiments of the invention are sensitive enough to assay targets at a concentration of $5 \times 10^{-9}$ M, preferably at a concentration of not more than $5 \times 10^{-10}$ M. Embodiments of the invention are sensitive enough to employ probes at a concentration of $5 \times 10^{-9}$ M, preferably at a concentration of not more than $5 \times 10^{-10}$ M. It should go without saying that the foregoing values are not intended to suggest that the method cannot detect higher concentrations.

The medium in which triplexes form can be any conventional medium known to be suitable for preserving nucleotides. See, e.g., Sambrook et al., "Molecular Cloning: A Lab Manual," Vol. 2 (1989). For example, the liquid medium can comprise nucleotides, water, buffers and standard salt concentrations. When divalent cations are used exclusively to promote triplex formation, chelators such as EDTA or EGTA should not be included in the reaction mixtures.

Specific binding between complementary bases occurs under a wide variety of conditions having variations in temperature, salt concentration, electrostatic strength, and buffer composition. Examples of these conditions and methods for applying them are known in the art.

Unlike many Hoogsteen-type triplexes, which are unstable or non-existent at pH levels above about 7.6, the Watson-Crick triplexes of the invention are stable over a wide range of pH levels, preferably from about pH 5 to about pH 9.

It is preferred that triplexes be formed at a temperature of about 5° C. to about 25° C. for about one hour or less. Longer reaction times are not required, but incubation for up to 24 hours in most cases did not adversely affect the triplexes. The fast binding times of Watson-Crick triplexes of the invention contrast with the much longer binding times for Hoogsteen triplex-based assays.

Although not required, it is possible to facilitate triplex formation in solution by using certain reagents in addition to cations. Preferred examples of these reagents include single stranded binding proteins such as Rec A protein, T4 gene 32 protein, E. coli single stranded binding protein, major or minor nucleic acid groove binding proteins, viologen and intercalating substances such as ethidium bromide, actinomycin D, psoralen, and angelicin. Such facilitating reagents may prove useful in extreme operating conditions, for example, under abnormal pH levels or extremely high temperatures.

The inventive assay can be used to, e.g., identify accessible regions in folded nucleotide sequences, to determine the number of mismatched base pairs in a hybridization complex, and to map genomes.

The inventors may sometimes herein suggest that Watson-Crick triplexes result from hybridization of the probe to duplex target. While fluorophores tethered to the probe produced quenched fluorescent emissions upon being exposed to duplex targets containing a strand of Watson-Crick complementary bases, which indicates the occurrence of some kind of binding event, the inventors are not sure that what occurs in the Watson-Crick triplex is best described as hybridization in the sense traditionally associated with Watson-Crick duplex formation. While the formation of a Watson-Crick triplex may sometimes be referred to as a hybridization event herein, that is merely for convenience and is not intended to limit the scope of the invention with respect to how the formation of a Watson-Crick triplex can be best characterized.

The invention will be illustrated in more detail with reference to the following Examples, but it should be understood that the present invention is not deemed to be limited thereto.

EXAMPLES

Example 1

Sense and antisense 50-mer ssDNA target sequences, derived from exon 10 of the human cystic fibrosis gene (Nature 380, 207 (1996)) were synthesized on a DNA synthesizer (Expedite 8909, PerSeptive Biosystems) and purified by HPLC. Equimolar amounts of complementary oligonucleotides were denatured at 95° C. for 10 min and allowed to anneal gradually as the temperature cooled to 21° C. over 1.5 hours. Double stranded DNA (dsDNA) oligonucleotides were dissolved in ddH$_2$O at a concentration of 1 pmole/μl.

Sequence for the sense strand of the wild-type target DNA (SEQ ID NO:1): 5'-TGG CAC CAT TAA AGA AAA TAT CAT CTT TGG TGT TTC CTA TGA TGA ATA TA-3'.

Sequence for the antisense strand of the wild-type target DNA (SEQ ID NO:1): 5'-TAT ATT CAT CAT AGG AAA CAC CAA AGA TGA TAT TTT CTT TAA TGG TGC CA-3'.

SEQ ID NO:2 was a 50-mer mutant dsDNA target sequence identical to wild-type target DNA (SEQ ID NO:1) except for a one base pair mutation (underlined) at amino acid position 507 at which the wild-type sequence CAT was changed to C<u>G</u>T.

Sequence for the sense strand of SEQ ID NO:2: 5'-TGG CAC CAT TAA AGA AAA TAT C<u>G</u>T CTT TGG TGT TTC CTA TGA TGA ATA TA-3'.

Sequence for the antisense strand of SEQ ID NO:2: 5'-TAT ATT CAT CAT AGG AAA CAC CAA AGA <u>C</u>GA TAT TTT CTT TAA TGG TGC CA-3'.

SEQ ID NO:3 was a 47-mer mutant dsDNA target sequence identical to wild-type target DNA (SEQ ID NO:l) except for a consecutive three base pair deletion (indicated by an ellipsis) at amino acid positions 507 and 508 at which the wild-type sequence CTT is deleted.

Sequence for the sense strand of SEQ ID NO:3: 5'-TGG CAC CAT TAA AGA AAA TAT CAT . . . TGG TGT TTC CTA TGA TGA ATA TA-3'.

Sequence for the antisense strand of SEQ ID NO:3: 5'-TAT ATT CAT CAT AGG AAA CAC CA . . . A TGA TAT TTT CTT TAA TGG TGC CA-3'.

Probe No. 1 (SEQ ID NO:4), a 15-mer ssDNA probe with an attached fluorescein moiety at the 5' position, was designed to be completely complementary to a 15 nucleotide segment of the sense strand of the 50-mer wild-type target DNA (SEQ ID NO:1), overlapping amino acid positions 505 to 510 (Nature 380, 207 (1996)). Probe No. 1 was synthesized on a DNA synthesizer, purified by HPLC, and dissolved in ddH$_2$O at a concentration of 1 pmole/μl.

Sequence for SEQ ID NO:4: 5'-Flu-CAC CAA AGA TGA TAT-3'.

The hybridization reaction mixture (40 μl) contained the following: 0.4 pmoles of target dsDNA, 4 pmoles of 5'-fluorescein labeled ssDNA Probe No. 1, 10 mM Tris-HCl, pH 7.5 and 0, 10, 25, 50, 75, 100, 125 or 150 mM NaCl. The reaction mixtures were incubated at room temperature (21° C.) for 1 hour, without prior denaturation. Samples were placed into a quartz cuvette, irradiated with an argon ion laser beam having a wavelength of 488 nm and monitored for fluorescent emission. The maximum fluorescent intensities occurred at a wavelength of 525 nm, the emission wavelength for fluorescein. The intensity of fluorescence was plotted as a function of wavelength for each sample analyzed.

In the absence of NaCl or presence of 10 mM or 25 mM NaCl, no hybridization between the dsDNA targets and the ssDNA-F probe was detected, resulting in similar fluorescent intensities observed when wild-type target SEQ ID NO:1 or mutant target SEQ ID NO:2 were mixed with Probe No. 1 (SEQ ID NO:4) or when Probe No. 1 was present alone (data not shown).

After a one-hour incubation at 21° C. in the presence of 50 mM NaCl, dsDNA:ssDNA-F triplexes consisting of perfectly complementary sequences (SEQ ID NO:1+Probe No. 1) formed readily, resulting in a 49% decrease in fluorescent intensity compared to that emitted by Probe No. 1 alone (labeled ssDNA-F) (FIG. 1A). In contrast, incompletely complementary dsDNA:ssDNA-F triplexes containing a 1 bp G-T mismatch (SEQ ID NO:2+Probe No. 1) were less stable in these reaction conditions, yielding only an 11% decrease in fluorescent intensity compared to that exhibited by Probe No. 1 alone.

Incubation for one hour in the presence of 75 mM NaCl was slightly less conducive to triplex formation, resulting in a 30% decrease in fluorescent intensity for the perfectly matched dsDNA:ssDNA-F triplex (FIG. 1B). Minimal formation of the 1 bp G-T mismatched dsDNA:ssDNA-F triplex was observed, resulting in only a 0.4% decrease in fluorescence.

The presence of 100 mM and 125 mM NaCl also facilitated maximum triplex DNA formation between the perfectly matched SEQ ID NO:1 target and Probe No. 1, and less stable triplex DNA formation between the 1 bp G-T mismatched SEQ ID NO:2 and Probe No. 1 hybrid (data not shown). At 150 mM NaCl, no triplex DNA formation was evident.

Therefore, the inclusion of monovalent cations such as Na$^+$ and K$^+$ at specific concentrations, was sufficient to allow detection of triplex formation between dsDNA targets and ssDNA probes labeled with fluorescein in the absence of prior denaturation. Moreover, the reaction occurred at room temperature within just one hour of incubation at a ratio of probe to target of 10 to 1, using natural dsDNA. The dsDNA targets and ssDNA probe used in this example contained a 33% GC content, and did not contain homopurine or homopyrimidine stretches of DNA. Despite the presence of 6 pyrimidine bases interspersed within the 15 nucleotide ssDNA probe, DNA triplexes formed easily. Significantly, the hybridization assay of the invention was able to discriminate between perfectly complementary DNA sequences and those containing a single 1 bp mismatch using natural DNA.

Example 2

To ensure that the hybridization assay, which used 5'-fluorescein labeled ssDNA probes and dsDNA targets in the absence of prior denaturation, would apply to probe and target DNAs possessing dramatically different percent GC contents (and potentially different annealing preferences), new 15-mer ssDNA-F probes and 50-mer dsDNA target sequences were synthesized, purified and annealed as above. Both ssDNA-F probes and dsDNA targets were dissolved in ddH$_2$O at a concentration of 1 pmole/μl.

SEQ ID NO:5 was a 50-mer dsDNA target sequence modified from SEQ ID NO:1, wherein the percent GC content was changed from 30% to 52%.

Sequence for the sense strand of the wild-type target DNA (SEQ ID NO:5): 5'-GAG CAC CAT GAC AGA CAC TGT CAT CTC TGG TGT GTC CTA CGA TGA CTC TG-3'.

Sequence for the antisense strand of the wild-type target DNA (SEQ ID NO:5): 5'-CAG AGT CAT CGT AGG ACA CAC CAG AGA TGA CAG TGT CTG TCA TGG TGC TC-3'.

SEQ ID NO:6 was a 50-mer mutant dsDNA target sequence identical to SEQ ID NO:5, except for a one base pair mutation (underlined), at which the sequence CTC was changed to CT_T_.

Sequence for the sense strand of mutant SEQ ID NO:6: 5'-GAG CAC CAT GAC AGA CAC TGT CAT CT_T_ TGG TGT GTC CTA CGA TGA CTC TG-3'.

Sequence for the antisense strand of mutant SEQ ID NO:6: 5'-CAG AGT CAT CGT AGG ACA CAC CA_A_ AGA TGA CAG TGT CTG TCA TGG TGC TC-3'.

SEQ ID NO:7 was a 50-mer mutant dsDNA target sequence identical to SEQ ID NO:5, except for a one base pair mutation (underlined), at which the sequence CAT was changed to C_G_T.

Sequence for the sense strand of mutant SEQ ID NO:7: 5'-GAG CAC CAT GAC AGA CAC TGT C_G_T CTC TGG TGT GTC CTA CGA TGA CTC TG-3'.

Sequence for the antisense strand of mutant SEQ ID NO:7: 5'-CAG AGT CAT CGT AGG ACA CAC CAG AGA _C_GA CAG TGT CTG TCA TGG TGC TC-3'.

SEQ ID NO:8 was a 50-mer mutant dsDNA target sequence identical to SEQ ID NO:5, except for a one base pair mutation (underlined), at which the sequence CAT was changed to C_T_T.

Sequence for the sense strand of mutant SEQ ID NO:8: 5'-GAG CAC CAT GAC AGA CAC TGT C_T_T CTC TGG TGT GTC CTA CGA TGA CTC TG-3'.

Sequence for the antisense strand of mutant SEQ ID NO:8: 5'-CAG AGT CAT CGT AGG ACA CAC CAG AGA _A_GA CAG TGT CTG TCA TGG TGC TC-3'.

SEQ ID NO:9 was a 50-mer mutant dsDNA target sequence identical to SEQ ID NO:5, except for a one base pair mutation (underlined), at which the sequence CTC was changed to C_C_C.

Sequence for the sense strand of mutant SEQ ID NO:9: 5'-GAG CAC CAT GAC AGA CAC TGT CAT C_C_C TGG TGT GTC CTA CGA TGA CTC TG-3'.

Sequence for the antisense strand of mutant SEQ ID NO:9: 5'-CAG AGT CAT CGT AGG ACA CAC CAG _G_GA TGA CAG TGT CTG TCA TGG TGC TC-3'.

SEQ ID NO:10 was a 50-mer mutant dsDNA target sequence identical to SEQ ID NO:5, except for a one base pair mutation (underlined), at which the sequence CTC was changed to C_G_C.

Sequence for the sense strand of mutant SEQ ID NO:10: 5'-GAG CAC CAT GAC AGA CAC TGT CAT C_G_C TGG TGT GTC CTA CGA TGA CTC TG-3'.

Sequence for the antisense strand of mutant SEQ ID NO:10: 5'-CAG AGT CAT CGT AGG ACA CAC CAG _C_GA TGA CAG TGT CTG TCA TGG TGC TC-3'.

SEQ ID NO:11 was a 50-mer mutant dsDNA target sequence identical to SEQ ID NO:5, except for a consecutive two base pair mutation (underlined), at which the sequence CAT was changed to _AC_T.

Sequence for the sense strand of mutant SEQ ID NO:11: 5'-GAG CAC CAT GAC AGA CAC TGT _AC_T CTC TGG TGT GTC CTA CGA TGA CTC TG-3'.

Sequence for the antisense strand of mutant SEQ ID NO:11: 5'-CAG AGT CAT CGT AGG ACA CAC CAG AGA _GT_A CAG TGT CTG TCA TGG TGC TC-3'.

SEQ ID NO:12 was a 50-mer dsDNA target sequence modified from SEQ ID NO:1, wherein the percent GC content was changed from 30% to 72%.

Sequence for the sense strand of the wild-type target DNA (SEQ ID NO:12): 5'-GAG CAC CCT CCC AGG CAC GGT CGT CCC TGG TGC GAC CTC CGA CGA GCG TG-3'.

Sequence for the antisense strand of the wild-type target DNA (SEQ ID NO:12): 5'-CAC GCT CGT CGG AGG TCG CAC CAG GGA CGA CCG TGC CTG GGA GGG TGC TC-3'.

SEQ ID NO:13 was a 50-mer mutant dsDNA target sequence identical to SEQ ID NO:12, except for a one base pair mutation (underlined), at which the sequence CGT was changed to C_A_T.

Sequence for the sense strand of mutant SEQ ID NO:13: 5'-GAG CAC CCT CCC AGG CAC GGT C_A_T CCC TGG TGC GAC CTC CGA CGA GCG TG-3'.

Sequence for the antisense strand of mutant SEQ ID NO:13: 5'-CAC GCT CGT CGG AGG TCG CAC CAG GGA _T_GA CCG TGC CTG GGA GGG TGC TC-3'.

Probe No. 2 (SEQ ID NO:14), a 15-mer ssDNA probe with an attached fluorescein moiety at the 5' position, was designed to be completely complementary to a 15 nucleotide segment of the sense strand of the 50-mer wild-type target DNA (SEQ ID NO:5).

Sequence for SEQ ID NO:14: 5'-Flu-CAC CAG AGA TGA CAG-3'.

Probe No. 3 (SEQ ID NO:15) was a 15-mer 5'-fluorescein labeled ssDNA probe designed to be completely complementary to a 15 nucleotide segment of the sense strand of the 50-mer wild-type target DNA (SEQ ID NO:12).

Sequence for SEQ ID NO:15: 5'-Flu-CAC CAG GGA CGA CCG-3'.

The triplex DNA hybridization assays performed in Example 1 were facilitated by the addition of monovalent cations in the reaction mixtures. The specificity of the hybridization assay was further examined utilizing divalent cations (instead of monovalent cations) to promote triplex DNA formation with dsDNA targets and ssDNA-F probes possessing various percent GC contents.

The hybridization reaction mixture (40 μl) contained the following: 0.4 pmoles of target dsDNA, 4 pmoles of 5'-fluorescein labeled ssDNA probe, 10 mM Tris-HCl, pH 7.5 and 5 mM to 30 mM MnCl$_2$ or 5 mM to 30 mM MgCl$_2$ or 5 mM to 30 mM NiCl$_2$. The reaction mixtures were incubated at room temperature (21° C.) for 1 hour, without prior denaturation. Samples were placed into a quartz cuvette, irradiated with an argon ion laser beam having a wavelength of 488 nm and monitored for fluorescent emission. The samples were saved and allowed to incubate at room temperature overnight for a total of 22 hours, at which time a second fluorescent intensity measurement was taken following irradiation with the argon ion laser beam. The intensity of fluorescence was plotted as a function of wavelength for each sample analyzed.

When the ssDNA-F Probe No. 2 (with a 53% GC content) was incubated with the 50-mer wild-type dsDNA target (SEQ ID NO:5) and mutant dsDNA targets (SEQ ID NO:6 to SEQ ID NO:11) in the presence of 10 mM MnCl$_2$, dsDNA:ssDNA-F triplexes were formed at room temperature under non-denaturing conditions. While perfectly matched DNA triplexes yielded the maximum decrease in fluorescent intensity (a 43% decrease after a one-hour incubation), the less stable dsDNA:ssDNA-F triplexes containing a 1 bp T-G mismatch (SEQ ID NO:6+Probe No. 2) produced a fluorescent intensity that was 20% lower than that observed with Probe No. 2 alone after a one-hour incubation (FIG. 2A). dsDNA:ssDNA-F triplexes that resulted in a 1 bp G-T mismatch (SEQ ID NO:7+Probe No. 2), a 1 bp T-T mismatch (SEQ ID NO:8+Probe No. 2), a 1 bp C-A mismatch (SEQ ID NO:9+Probe No. 2) and a consecutive 2 bp A-G and C-T mismatch (SEQ ID NO:11+Probe No. 2) were all less stable than the perfectly matched DNA triplex (SEQ ID NO:5+Probe No. 2) yielding fluorescent intensities in between that observed for Probe No. 2 alone and that observed for the perfectly matched DNA triplex (data not shown). Except for the 1 bp T-T mismatched DNA triplex, which was the least stable (resulting in only a 5% decrease in fluorescent intensity after 1 hour), all of the other mismatched DNA triplexes generated very similar fluorescent intensities. Only the dsDNA:ssDNA-F triplex that contained a 1 bp G-A mismatch (SEQ ID NO:10+Probe No. 2) yielded a fluorescent intensity lower than that produced by the perfectly matched DNA triplex (data not shown).

DNA triplex formation was more efficient after a 22-hour incubation in the presence of 10 mM MnCl$_2$. Nevertheless, a more prominent discrimination between DNA triplexes containing perfectly matched sequences and DNA triplexes containing base pair mismatched sequences was observed. As illustrated in FIG. 2B, the dsDNA:ssDNA-F triplexes containing perfectly complementary sequences (SEQ ID NO:5+Probe No. 2) or a 1 bp T-G mismatch (SEQ ID NO:6+Probe No. 2) produced fluorescent intensities that were 92% and 66% lower, respectively, than the intensity achieved by Probe No. 2 alone, following a 22-hour incubation in the presence of 10 mM MnCl$_2$. Similarly, incubation in the presence of 30 mM MnCl$_2$ for 22 hours, resulted in a 90% and a 57% reduction in fluorescent intensity for perfectly matched DNA triplexes and 1 bp T-G mismatched DNA triplexes, respectively (FIG. 2C).

The inclusion of 20 mM MgCl$_2$ or 20 mM MnCl$_2$ or 20 mM NiCl$_2$ also facilitated dsDNA:ssDNA triplex formation when the ssDNA-F Probe No. 3 (possessing a 73% GC content) was reacted with the corresponding 50-mer wild-type dsDNA target (SEQ ID NO:12) and mutant dsDNA target (SEQ ID NO:13) for one hour (data not shown). As expected, the perfectly matched DNA triplexes generated the maximum decreases in fluorescent intensity, while the less stable 1 bp A-C mismatched DNA triplexes (SEQ ID NO: 13+Probe No. 3) produced intermediate levels of fluorescence (data not shown). The perfectly matched DNA triplexes formed very efficiently in the presence of 10 mM MnCl$_2$ after a 22 hour incubation, yielding an 89% decrease in fluorescent intensity. The 1 bp A-C mismatched DNA triplexes were formed with equal efficiency in these reaction conditions, generating a 90% decrease in fluorescence compared to that observed with Probe No. 3 alone (data not shown). Therefore, better discrimination was achieved between the perfectly matched and 1 bp mismatched 73% GC DNA triplexes following short incubation times of 1 hour in the presence of 20 mM divalent cations.

Perfectly matched dsDNA:ssDNA-F triplexes (possessing a 33% GC content) (SEQ ID NO:1+Probe No. 1) formed readily within 1 hour in the presence of 10 mM MnCl$_2$, resulting in a 57% decrease in fluorescent intensity compared to that emitted by Probe No. 1 alone (data not shown). These reaction conditions were highly unfavorable for DNA triplexes that contained a 1 bp G-T mismatch (SEQ ID NO:2+Probe No. 1), resulting in an increased fluorescence compared to that observed by Probe No. 1 alone (data not shown). Similar results were obtained following a 22 hour incubation in the presence of 15 mM MgCl$_2$.

Regardless of the percent GC content of the dsDNA targets and ssDNA probes, the addition of divalent cations such as $Mn^{+2}$, $Mg^{+2}$ or $Ni^{+2}$ promoted DNA triplex formation under non-denaturing conditions, to allow accurate discrimination between perfectly complementary sequences and those containing 1 bp mutations.

Example 3

The triplex DNA hybridization assays in Examples 1 and 2 were performed in the presence of one type of monovalent or divalent cation. The next examples will demonstrate the reliability of the assay of the invention to differentiate between perfect matches and 1 bp mismatches in triplex DNA when combinations of divalent cations are present in the reaction mixtures.

The hybridization reaction mixture (40 μl) contained the following: 0.4 pmoles of target dsDNA, 4 pmoles of 5'-fluorescein labeled ssDNA probe, 10 mM Tris-HCl, pH 7.5 and 5 mM MgCl$_2$ and 5 mM MnCl$_2$, or 10 mM MgCl$_2$ and 10 mM MnCl$_2$, or 15 mM MgCl$_2$ and 15 mM MnCl$_2$, or 20 mM MgCl$_2$ and 20 mM MnCl$_2$. The reaction mixtures were incubated at room temperature (21° C.) for 1 hour, without prior denaturation. Samples were placed into a quartz cuvette, irradiated with an argon ion laser beam having a wavelength of 488 nm and monitored for fluorescent emission. The samples were saved and allowed to incubate at room temperature overnight for a total of 22 hours, at which time a second fluorescent intensity measurement was taken following irradiation with the argon ion laser beam. The intensity of fluorescence was plotted as a function of wavelength for each sample analyzed.

In all mixtures of dsDNA target and ssDNA-F probe, the addition of 5 mM MgCl$_2$ and 5 mM MnCl$_2$ was insufficient to allow detection of triplex DNA formation (data not shown). When the ssDNA-F Probe No. 3 (with a 73% GC content) was incubated for one hour with the 50-mer wild-type dsDNA target (SEQ ID NO:12) in the presence of 10 mM MgCl$_2$ and 10 mM MnCl$_2$, or 15 mM MgCl$_2$ and 15 mM MnCl$_2$, perfectly complementary dsDNA:ssDNA-F triplexes were formed with equal efficiency, generating a 29% decrease in fluorescence compared to that emitted by Probe No. 3 alone. Both reaction conditions were highly unfavorable for DNA triplexes that contained a 1 bp A-C mismatch (SEQ ID NO:13+Probe No. 3), resulting in a 14% increase in fluorescence compared to that observed with Probe No. 3 alone. The fluorescent spectra obtained after a one hour incubation in the presence of 15 mM $MgCl_2$ and 15 mM $MnCl_2$ are shown in FIG. 3A.

Incubation for 22 hours yielded more DNA triplex formation. The dsDNA:ssDNA-F triplexes containing perfectly matched sequences (SEQ ID NO:12+Probe No. 3) or a 1 bp A-C mismatch (SEQ ID NO:13+Probe No. 3) produced fluorescent intensities that were 62% and 21% lower, respectively, than that achieved by Probe No. 3 alone, following a 22 hour incubation in the presence of 10 mM $MgCl_2$ and 10 mM $MnCl_2$ (FIG. 3B). Very similar results were obtained with the samples containing 15 mM $MgCl_2$ and 15 mM $MnCl_2$ after 22 hours (data not shown).

Treatment with 20 mM $MgCl_2$ and 20 mM $MnCl_2$ for just one hour, resulted in a 46% and a 3% reduction in fluorescence for perfectly matched DNA triplexes and 1 bp A-C mismatched DNA triplexes, respectively (FIG. 3C). In this case, no benefit was achieved by further incubating the samples for 22 hours (data not shown).

When dsDNA targets containing a 73% GC content are tested in the hybridization assay of the invention, a one-hour treatment with 20 mM $MgCl_2$ and 20 mM $MnCl_2$ provides the maximum difference in stability and fluorescence between perfectly complementary DNA triplexes and DNA triplexes containing a 1 bp mismatch.

Example 4

When the ssDNA-F Probe No. 1 (with a 33% GC content) was incubated with the wild-type dsDNA target (SEQ ID NO:1) or mutant dsDNA targets (SEQ ID NO:2 and SEQ ID NO:3), in the presence of 10 mM $MgCl_2$ and 10 mM $MnCl_2$, minimal DNA triplex formation was observed (data not shown). However, incubation in the presence of 15 mM $MgCl_2$ and 15 mM $MnCl_2$ for one hour facilitated perfectly matched DNA triplex formation, as evidenced by the 49% decrease in fluorescent intensity observed, compared to that obtained by Probe No. 1 (FIG. 4A). dsDNA:ssDNA-F triplexes that resulted in a 1 bp G-T mismatch (SEQ ID NO:2+Probe No. 1) or a 3 bp deletion (SEQ ID NO:3+Probe No. 1) were very unstable in the presence of 15 mM $MgCl_2$ and 15 mM $MnCl_2$, yielding a 2% decrease in fluorescence and a 5% increase in fluorescence, respectively, compared to that emitted by Probe No. 1 alone (FIG. 4A).

Treatment with 20 mM $MgCl_2$ and 20 mM $MnCl_2$ for 1 hour, resulted in a 68%, a 48% and a 6% reduction in fluorescence for perfectly matched DNA triplexes, and for dsDNA:ssDNA-F triplexes containing a 1 bp G-T mismatch or a 3 bp deletion, respectively, compared to that observed with Probe No. 1 alone (FIG. 4B). Optimum discrimination between the 33% GC DNA triplexes containing wild-type sequences or base pair mismatches was achieved when these same samples were incubated for 22 hours. The perfectly complementary DNA triplexes (SEQ ID NO:1+Probe No. 1) remained stable over the 22 hours, producing a 62% decrease in fluorescent intensity, compared to that achieved by Probe No. 1 alone (FIG. 4C). By contrast, the dsDNA:ssDNA-F triplexes containing a 1 bp G-T mismatch (SEQ ID NO:2+Probe No. 1) or a 3 bp deletion (SEQ ID NO:3+Probe No. 1) proved to be very unstable during the 22 hour incubation, generating a 1% and a 13% increase in fluorescence, respectively, compared to that emitted by Probe No. 1 alone (FIG. 4C).

Example 5

Perfectly matched dsDNA:ssDNA-F triplexes (possessing a 53% GC content) (SEQ ID NO:5+Probe No. 2) formed readily within one hour in the presence of 10 MM $MgCl_2$ and 10 mM $MnCl_2$, resulting in a 68% decrease in fluorescence compared to that observed by Probe No. 2 alone (FIG. 5A). The DNA triplexes that contained a 1 bp T-G mismatch (SEQ ID NO:6+Probe No. 2) were less stable, generating a 20% decrease in fluorescent intensity compared to that achieved by Probe No. 2 alone (FIG. 5A).

Incubation of the same samples for 22 hours produced an even more dramatic difference in fluorescence achieved by the perfectly matched or mismatched DNA triplexes. As illustrated in FIG. 5B, the dsDNA:ssDNA-F triplexes containing perfectly complementary sequences (SEQ ID NO:5+Probe No. 2) or a 1 bp T-G mismatch (SEQ ID NO:6+Probe No. 2) generated fluorescent intensities that were 92% and 33% lower, respectively, than that emitted by Probe No. 2 alone, in the presence of 10 mM $MgCl_2$ and 10 mM $MnCl_2$.

In a similar experiment, while the perfectly matched DNA triplex (SEQ ID NO:5+Probe No. 2) yielded a 85% decrease in fluorescence compared to that observed with Probe No. 2 alone following a 22 hour incubation in the presence of 10 mM $MgCl_2$ and 10 mM $MnCl_2$, the dsDNA:ssDNA-F triplexes that resulted in a 1 bp G-T mismatch (SEQ ID NO:7+Probe No. 2), a 1 bp C-A mismatch (SEQ ID NO:9+Probe No. 2) and a consecutive 2 bp A-G and C-T mismatch (SEQ ID NO:11+Probe No. 2) produced a 43%, a 69% and a 32% reduction in fluorescence (FIG. 5C). Only the dsDNA:ssDNA-F triplex that contained a 1 bp G-A mismatch (SEQ ID NO:10+Probe No. 2) yielded a fluorescent intensity slightly lower than that produced by the perfectly matched DNA triplex (data not shown).

Optimum discrimination between the 53% GC DNA triplexes containing perfectly complementary sequences or base pair mismatches was achieved following a one-hour incubation in the presence of 15 mM $MgCl_2$ and 15 mM $MnCl_2$. These reaction conditions greatly facilitated DNA triplex formation between the perfectly matched DNA sequences (SEQ ID NO:5+Probe No. 2), resulting in a 74% reduction in fluorescence compared to that achieved by Probe No. 2 alone (FIG. 5D). By contrast, dsDNA:ssDNA-F triplexes that contained a 1 bp T-G mismatch (SEQ ID NO:6+Probe No. 2) were much less stable in the presence of 15 mM $MgCl_2$ and 15 mM $MnCl_2$, yielding a 15% decrease in fluorescence compared to that emitted by Probe No. 2 alone after a one-hour incubation (FIG. 5D).

Similarly, DNA triplexes that resulted in a 1 bp G-T mismatch (SEQ ID NO:7+Probe No. 2), a 1 bp C-A mismatch (SEQ ID NO:9+Probe No. 2), a 1 bp G-A mismatch (SEQ ID NO:10+Probe No. 2) and a consecutive 2 bp A-G and C-T mismatch (SEQ ID NO:11+Probe No. 2) were all much less stable than the perfectly matched DNA triplex (data not shown). The 1 bp G-A mismatched DNA triplex that formed relatively easily in the presence of 10 mM $MnCl_2$ or 10 mM $MgCl_2$ and 10 mM $MnCl_2$, was now disrupted in the presence of 15 mM $MgCl_2$ and 15 mM $MnCl_2$, producing only a 7% reduction in fluorescence compared to that observed with Probe No. 2 alone (data not shown). When Probe No. 2 (containing a 53% GC content) was reacted with the dsDNA target SEQ ID NO:3 (containing a 33% GC content), a 3% increase in fluorescence was observed compared to that obtained by Probe No. 2 alone (FIG. 5D), indicative of no DNA triplex formation. This result was expected considering this probe and target combination would result in a 5 bp mismatch.

Treatment with 15 mM $MgCl_2$ and 15 mM $MnCl_2$ for 22 hours, generated a 76% and a 44% decrease in fluorescence intensity for dsDNA:ssDNA-F triplexes containing perfectly complementary sequences (SEQ ID NO:5+Probe No. 2) and a 1 bp T-G mismatch (SEQ ID NO:6+Probe No. 2), respectively, compared to that obtained with Probe No. 2 alone (FIG. 5E).

Collectively, the above Examples demonstrated that the addition of at least one type of cation to a hybridization medium promotes DNA triplex formation between dsDNA targets and fluorescently-labeled ssDNA probes, possessing dramatically different percent GC contents, to allow accurate and reliable discrimination between perfectly complementary sequences and those containing various mutations.

While the invention has been described in detail and with reference to specific examples thereof, it will be apparent to one skilled in the art that various changes and modifications can be made therein without departing from the spirit and scope thereof.

What is claimed is:

1. A Watson-Crick triplex complex comprising a single-stranded probe bound to a double-stranded nucleic acid target, wherein: (a) said probe comprises a heteropolymeric nucleic acid or a heteropolymeric nucleic acid analog, (b) said triplex complex comprises base triplets, (c) all said base triplets of said complex are members selected from the group consisting of A-T-A, T-A-T, U-A-T, T-A-U, A-U-A, U-A-U, G-C-G and C-G-C, (d) at least one of said base triplets is A-T-A, A-U-A or G-C-G, (e) at least one other of said base triplets is T-A-T, U-A-T, T-A-U, U-A-U or C-G-C, and (f) the triplex complex is isolated, the triplex complex is purified, the probe is synthetic and/or the target is synthetic.

2. The complex of claim 1, wherein a pH of a medium in which said complex is present is greater than 7.6.

3. The complex of claim 1, wherein said single-stranded probe is 5 to 30 bases long and said double-stranded nucleic acid target is 8 to $3.3 \times 10^9$ base pairs long.

4. The complex of claim 1, wherein said target sequence contains 25% to 75% purin bases and 75% to 25% pyrimidine bases in any order.

5. The complex of claim 1, wherein said probe is covalently bound to a double-stranded nucleic acid cleaving agent.

6. The complex of claim 1, wherein said probe is covalently bound to a chemotherapeutic agent.

7. The complex of claim 1, wherein said probe is covaleatly bound to a label.

8. The complex of claim 7, wherein said label is a multi-molecule signaling complex, a redox pair, a chemiluminescent agent or an electrochemiluminescent agent.

9. The complex of claim 7, wherein said label is a fluorophore.

10. The complex of claim 9, wherein a fluorescent intensity of said complex is directly correlated with a binding affinity between said probe and said target sequence.

11. The complex of claim 1, wherein said triplex complex further comprises at least one base pair mismatch between said single-stranded probe and said double-stranded target.

12. The complex of claim 1, wherein said triplex complex further comprises 1 to 3 base pair mismatches between said single-stranded probe and said double-stranded target.

13. A Watson-Crick triplex complex comprising a single-stranded probe bound to a double-stranded nucleic acid target, wherein: (a) said probe comprises a heteropolymeric nucleic acid or a heteropolymeric nucleic acid analog; (b) said triplex complex comprises base triplets; (c) all said base triplets of said complex are members selected from the group consisting of A-T-A, T-A-T, U-A-T, T-A-U, A-U-A, U-A-U, G-C-G and C-G-C; (d) at least one of said base triplets is A-T-A, A-U-A or G-C-G; (e) at least one other of said base triplets is T-A-T, U-A-T, T-A-U, U-A-U or C-G-C; (f) said single-stranded probe is 5 to 30 bases long; (g) said double-stranded nucleic acid target is 8 to $3.3 \times 10^9$ base pairs long; and (h) the triplex complex is isolated, the triplex complex is purified, the probe is synthetic and/or the target is synthetic.

14. The complex of claim 13, wherein the complex is prepared by a process comprising contacting the probe with the target in the presence of a cation.

15. A Watson-Crick triplex complex comprising a single-stranded probe bound to a double-stranded nucleic acid target, wherein: (a) said target contains a target sequence containing at least one purine base and at least one pyrimidine base; (b) said probe comprises a heteropolymeric nucleic acid or a heteropolymeric nucleic acid analog sequence at least partially complementary to said target sequence, and containing at least one purine base and at least one pyrimidine base; (c) said triplex complex further comprises base triplets; (d) all said base triplets of said complex are members selected from the group consisting of A-T-A, T-A-T, U-A-T, T-A-U, A-U-A, U-A-U, G-C-G and C-G-C; (e) at least one of said base triplets is A-T-A, A-U-A or G-C-G; (f) at least one other of said base triplets is T-A-T, U-A-T, T-A-U, U-A-U or C-G-C; (g) the complex is prepared by a process comprising contacting the probe with the target in the presence of a cation; and (h) the triplex complex is isolated, the triplex complex is purified, the probe is synthetic and/or the target is synthetic.

16. The complex of claim 15, wherein said single-stranded probe is 5 to 30 bases long and said double-stranded nucleic acid target is 8 to $3.3 \times 10^9$ base pairs long.

* * * * *